United States Patent
Zhou et al.

(10) Patent No.: US 10,803,984 B2
(45) Date of Patent: Oct. 13, 2020

(54) MEDICAL IMAGE PROCESSING APPARATUS AND MEDICAL IMAGE PROCESSING SYSTEM

(71) Applicant: Canon Medical Systems Corporation, Otawara-shi (JP)

(72) Inventors: Jian Zhou, Buffalo Grove, IL (US); Zhou Yu, Glenview, IL (US); Yan Liu, Vernon Hills, IL (US)

(73) Assignee: Canon Medical Systems Corporation, Otawara-shi (JP)

(*) Notice: Subject to any disclaimer, the term of this patent is extended or adjusted under 35 U.S.C. 154(b) by 0 days.

(21) Appl. No.: 16/143,161

(22) Filed: Sep. 26, 2018

(65) Prior Publication Data
US 2019/0108904 A1  Apr. 11, 2019

Related U.S. Application Data

(63) Continuation-in-part of application No. 15/727,216, filed on Oct. 6, 2017.

(51) Int. Cl.
*G16H 30/20* (2018.01)
*G06T 5/00* (2006.01)
(Continued)

(52) U.S. Cl.
CPC ........... *G16H 30/20* (2018.01); *G06K 9/6298* (2013.01); *G06K 9/66* (2013.01); *G06K 9/6814* (2013.01);
(Continued)

(58) Field of Classification Search
CPC ......... G06T 7/0012; G06T 2207/20081; G06T 2207/10081; G06T 2207/30004;
(Continued)

(56) References Cited

U.S. PATENT DOCUMENTS 5,305,204 A * 4/1994 Ohhashi .................. G06T 5/009
382/131
5,406,479 A * 4/1995 Harman ............... G01N 23/046
378/7
(Continued)

FOREIGN PATENT DOCUMENTS

CN       106940816 A       7/2017
WO    2017/106645 A1    6/2017

OTHER PUBLICATIONS

Extended European Search Report dated Feb. 26, 2019 in European Patent Application No. 18198432.9, 11 pages.
(Continued)

*Primary Examiner* — Aklilu K Woldemariam
(74) *Attorney, Agent, or Firm* — Oblon, McClelland, Maier & Neustadt, L.L.P.

(57) ABSTRACT

A medical image processing apparatus according to an embodiment comprises a memory and processing circuitry. The memory is configured to store a plurality of neural networks corresponding to a plurality of imaging target sites, respectively, the neural networks each including an input layer, an output layer, and an intermediate layer between the input layer and the output layer, and each generated through learning processing with multiple data sets acquired for the corresponding imaging target site. The processing circuitry is configured to process first data into second data using, among the neural networks, the neural network corresponding to the imaging target site for the first data, wherein the first data is input to the input layer and the second data is output from the output layer.

16 Claims, 19 Drawing Sheets

(51) Int. Cl.
| | |
|---|---|
| G06T 5/50 | (2006.01) |
| G06T 11/00 | (2006.01) |
| G06T 7/00 | (2017.01) |
| G06K 9/62 | (2006.01) |
| G06K 9/68 | (2006.01) |
| G06K 9/66 | (2006.01) |
| G06N 3/08 | (2006.01) |

(52) U.S. Cl.
CPC ............. *G06N 3/08* (2013.01); *G06T 5/002* (2013.01); *G06T 5/50* (2013.01); *G06T 7/0014* (2013.01); *G06T 11/003* (2013.01); *G06T 11/008* (2013.01); *G06T 2207/10081* (2013.01); *G06T 2207/10088* (2013.01); *G06T 2207/10104* (2013.01); *G06T 2207/10108* (2013.01); *G06T 2207/20081* (2013.01); *G06T 2207/20084* (2013.01); *G06T 2207/30004* (2013.01)

(58) Field of Classification Search
CPC ......... G06T 2207/10088; G06T 11/005; G06T 5/009; G06T 2207/10116; G06T 5/40; G06T 2207/10072; G06T 7/0002; A61B 5/05; A61B 5/7221; A61B 8/5261; A61B 2090/3762; A61B 5/0036; A61B 6/507; A61B 6/5223; A61B 5/444; A61B 90/361; A61B 5/7264; A61B 2090/363; A61B 2090/364; A61B 5/0013; A61B 5/0022; A61B 5/441; A61B 6/12; A61B 8/4438; A61B 1/0005; A61B 1/05; A61B 2034/2065; A61B 2576/00; A61B 5/08; A61B 5/1128; A61B 90/37; A61B 6/032; A61B 6/563; G16H 30/40; G16H 30/20; G16H 50/20; G16H 40/40; G06N 3/08; G06N 20/10; G06N 5/003; G06N 20/00; G06K 9/6298; G06K 9/66; G06K 9/6256; G06K 9/627; G06K 9/00127; G06K 9/6267; G06F 19/00; G06F 19/321; G06F 2207/4824; A61N 5/1031; A61N 5/1039
USPC ........ 382/128, 129, 130, 131, 132; 600/200, 600/473, 476
See application file for complete search history.

(56) References Cited

U.S. PATENT DOCUMENTS

| | | | | |
|---|---|---|---|---|
| 5,640,261 | A * | 6/1997 | Ono ................... | G06N 3/0675 359/107 |
| 7,417,440 | B2 * | 8/2008 | Peschmann .......... | G01V 5/0016 250/250 |
| 9,233,645 | B2 * | 1/2016 | Schofield ........... | G02B 27/0101 |
| 2003/0007674 | A1 * | 1/2003 | Tsujii .................... | G06T 7/0012 382/132 |
| 2003/0209893 | A1 * | 11/2003 | Breed ...................... | B60J 10/00 280/735 |
| 2004/0129478 | A1 * | 7/2004 | Breed ..................... | B60N 2/002 180/273 |
| 2004/0130442 | A1 * | 7/2004 | Breed ...................... | B60C 11/24 340/443 |
| 2005/0046584 | A1 * | 3/2005 | Breed ..................... | E05F 15/43 340/13.31 |
| 2005/0131607 | A1 * | 6/2005 | Breed ..................... | B60N 2/002 701/45 |
| 2005/0152592 | A1 * | 7/2005 | Kasai .................... | G06T 7/0012 382/132 |
| 2009/0030295 | A1 * | 1/2009 | Shioi ..................... | A61B 1/227 600/316 |
| 2009/0169075 | A1 * | 7/2009 | Ishida ................... | G06T 7/0012 382/128 |
| 2009/0318815 | A1 * | 12/2009 | Barnes ................. | A61B 5/0064 600/473 |
| 2011/0301441 | A1 * | 12/2011 | Bandic ................. | A61B 5/0059 600/306 |
| 2012/0168607 | A1 * | 7/2012 | Okhmatovski ....... | A61B 5/0507 250/206 |
| 2012/0183187 | A1 * | 7/2012 | Sasaki ................... | G16H 50/20 382/128 |
| 2013/0071876 | A1 * | 3/2013 | Hao ....................... | G01N 23/04 435/40.52 |
| 2013/0182927 | A1 * | 7/2013 | Jang ..................... | G06T 11/006 382/131 |
| 2013/0289424 | A1 * | 10/2013 | Brockway ............ | A61B 5/0015 600/509 |
| 2013/0336553 | A1 * | 12/2013 | Buisseret .............. | G06T 7/12 382/128 |
| 2015/0065803 | A1 * | 3/2015 | Douglas ................ | G06T 7/11 600/200 |
| 2016/0174902 | A1 * | 6/2016 | Georgescu ........... | A61B 5/7267 600/408 |
| 2017/0046616 | A1 | 2/2017 | Socher et al. | |
| 2017/0064333 | A1 * | 3/2017 | Kim ...................... | H04N 19/60 |
| 2017/0206635 | A1 * | 7/2017 | Yu ......................... | G06T 5/00 |
| 2017/0372456 | A1 * | 12/2017 | Lee ...................... | G06T 5/002 |
| 2018/0060723 | A1 * | 3/2018 | Nakano ................ | G06N 3/0454 |
| 2018/0061059 | A1 * | 3/2018 | Xu ........................ | G06N 3/084 |
| 2018/0144214 | A1 | 5/2018 | Hsieh et al. | |
| 2018/0144243 | A1 * | 5/2018 | Hsieh ................... | G06N 3/0454 |
| 2018/0144465 | A1 * | 5/2018 | Hsieh .................... | G06N 3/08 |
| 2018/0144466 | A1 * | 5/2018 | Hsieh ................... | G06T 7/0012 |
| 2019/0192880 | A1 * | 6/2019 | Hibbard ............... | G06N 3/0454 |
| 2019/0244399 | A1 * | 8/2019 | Li ......................... | G01R 33/5611 |

OTHER PUBLICATIONS

Würfl, T., et al., "Deep Learning Computed Tomography", International Conference on Simulation, Modeling, and Programming for Autonomous Robots, XP047364505, Oct. 2, 2016, pp. 432-440.

Lai, M., "Deep Learning for Medical Image Segmentation", Retrieved from the Internet: URL: https://arxiv.org/pdf/1505.02000v1.pdf, XP055550857, Apr. 29, 2015, pp. 1-23.

Agostinelli, F., et al., "Adaptive Multi-Column Deep Neural Networks with Application to Robust Image Denoising", NIPS'13 Proceedings of the 26th International Conference on Neural Information Processing Systems, XP055508282, Dec. 10, 2013, 9 pages.

Wang, G., "A Perspective on Deep Imaging", IEEE Access, vol. 4, XP55451413, Jan. 1, 2016, pp. 8914-8924.

Ghaemmaghami, M.P., et al., "Robust Speech Recognition Using MLP Neural Network in Log-Spectral Domain", Signal Processing and Information Technology, 2009 IEEE International Symposium, XP031624810, Dec. 14, 2009, pp. 467-472.

Sam, D.B., et al., "Switching Convolutional Neural Network for Crowd Counting", 2017 IEEE Conference on Computer Vision and Pattern Recognition, XP033249755, Jul. 21, 2017, pp. 4031-4039.

Bahloul, M.R., et al., "Modulation Classification for MIMO systems: State of the art and research directions", Chaos, Solitons and Fractals, vol. 89, XP029566529, Mar. 22, 2016, pp. 497-505.

Moeskops et al., "Deep Learning for Multi-Task Medical Image Segmentation in Multiple Modalities," Medical Image Computing and Computer-Assisted Intervention—MICCAI, 2016, Part II, LNCS 9901, pp. 478-486.

Shen et al., "Deep Learning in Medical Image Analysis," Annu Rev Biomed Eng., Jun. 21, 2017.

Office Action dated Apr. 10, 2019 in U.S. Appl. No. 15/727,216, 35 pages.

U.S. Office Action dated Apr. 6, 2020 in U.S. Appl. No. 15/727,216, citing document AA therein, 32 pages.

\* cited by examiner

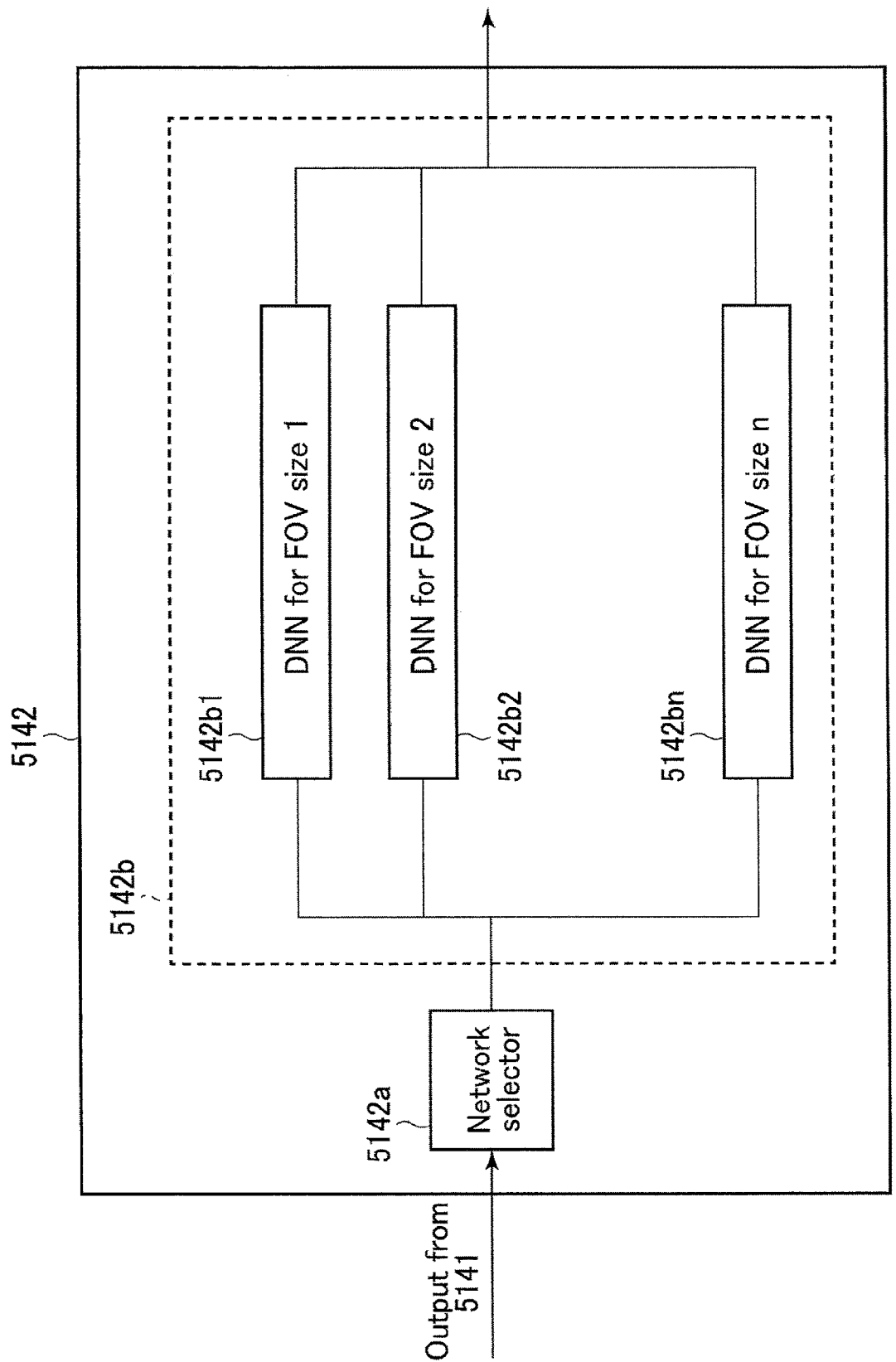
F I G. 11

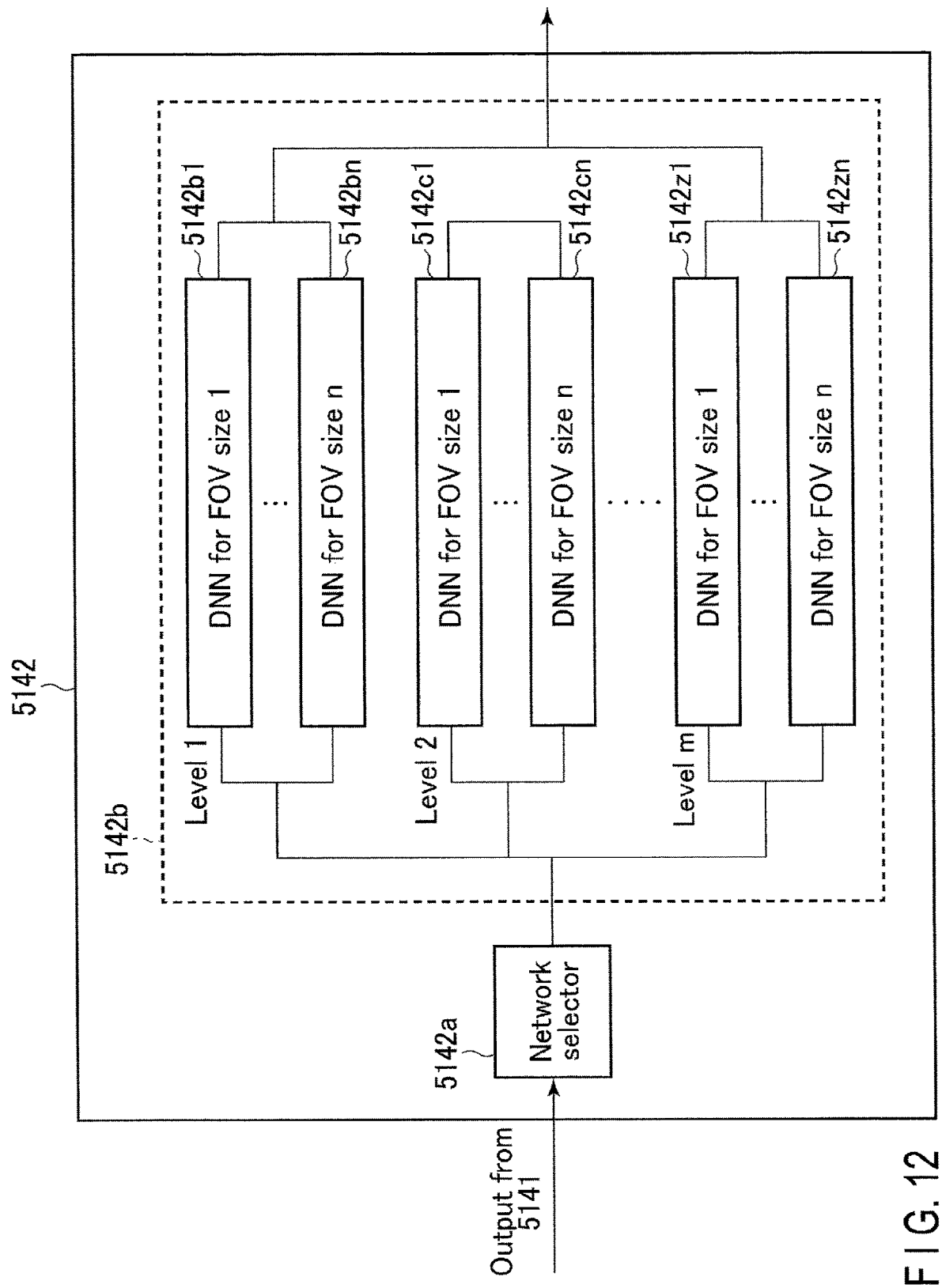
F I G. 12

MEDICAL IMAGE PROCESSING APPARATUS AND MEDICAL IMAGE PROCESSING SYSTEM

CROSS-REFERENCE TO RELATED APPLICATIONS

This application is a continuation in part based upon and claims the benefit of priority from the prior American patent application Ser. No. 15/727,216, filed Oct. 6, 2017, the entire contents which are incorporated herein by reference.

FIELD

Embodiments described herein relate generally to a medical image processing apparatus and a medical image processing system.

BACKGROUND

Computed tomography (CT) systems and methods are widely used, particularly for medical imaging and diagnosis. CT systems generally create images of one or more sectional slices through a subject's body. A radiation source, such as an X-ray source, irradiates the body from one side. At least one detector on the opposite side of the body receives radiation transmitted through the body. The attenuation of the radiation that has passed through the body is measured by processing electrical signals received from the detector.

A CT sinogram indicates attenuation through the body as a function of position along a detector array and as a function of the projection angle between the X-ray source and the detector array for various projection measurements. In a sinogram, the spatial dimensions refer to the position along the array of X-ray detectors. The time/angle dimension refers to the projection angle of X-rays, which changes as a function of time during a CT scan. The attenuation resulting from a portion of the imaged object (e.g., a vertebra) will trace out a sine wave around the vertical axis. Those portions farther from the axis of rotation correspond to sine waves with larger amplitudes, and the phase of the sine waves corresponds to the angular positions of objects around the rotation axis. Performing an inverse Radon transform—or any other image reconstruction method—reconstructs an image from the projection data in the sinogram.

X-ray CT has found extensive clinical applications in cancer, heart, and brain imaging. As CT has been increasingly used for a variety of applications including, e.g., cancer screening and pediatric imaging, there has arisen a push to reduce the radiation dose of clinical CT scans to become as low as reasonably achievable. For low-dose CT, the image quality can be degraded by many factors, such as high quanta noise challenge scanning geometry (i.e., large cone angle, high helical pitch, truncation, etc.), and other non-ideal physical phenomenon (i.e., scatter, beam hardening, crosstalk, metal, etc.). Developing efficient correction methods can be challenging due to the difficulties of modelling accurate forward model and solving complicated inverse problem.

Although many cutting-edge technologies have been developed during the past decades to improve low-dose CT image quality, such as model based iterative image reconstruction or sinogram restoration, those methods are often time consuming and require expensive hardware. Particularly, at some challenge scenarios, the image qualities are still inferior to the high dose images. Accordingly, improved methods are desired in order to reduce computational time, hardware costs and further improve low-dose CT image quality.

In view of the circumstances discussed above, the objects of the embodiments include providing a medical image processing apparatus and a medical image processing system that are capable of improving image qualities, accelerating processing speeds, and reducing hardware costs from those of the conventional apparatuses and systems.

BRIEF DESCRIPTION OF THE DRAWINGS

FIG. 11 is a block diagram showing an exemplary overview configuration of a denoise processor according to the second embodiment.

FIG. 12 is a block diagram showing another exemplary overview configuration of the denoise processor according to the second embodiment.

DETAILED DESCRIPTION

Figure 1A:
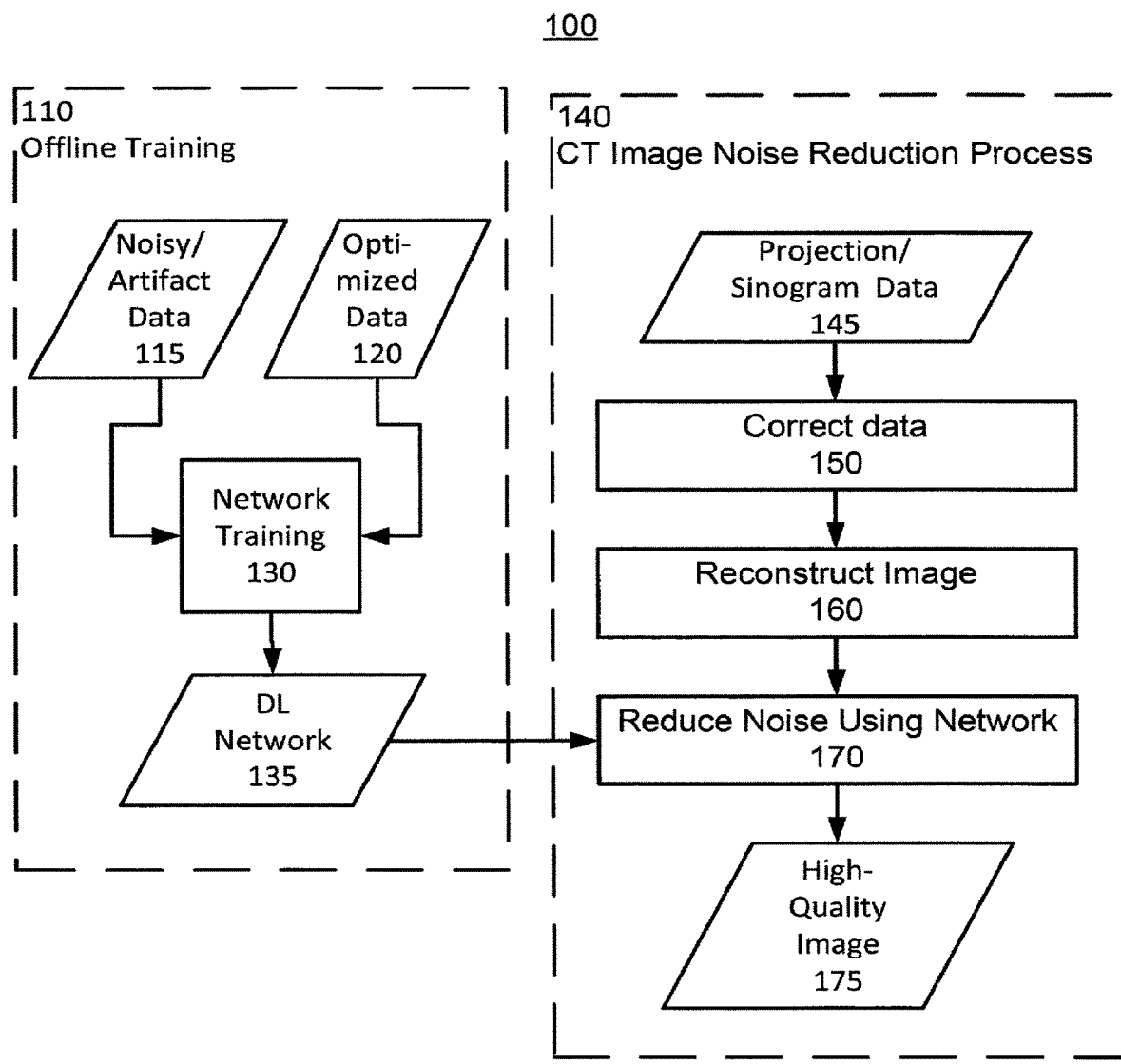
FIG. 1A shows an example of a flow diagram of a method for reducing noise and/or an artifact that uses a deep-learning (DL) network to process a reconstructed image, according to one implementation.

A medical image processing apparatus according to an embodiment includes a memory and processing circuitry.

The memory stores a plurality of neural networks corresponding to a plurality of imaging target sites, respectively. The neural networks each include an input layer, an output layer, and an intermediate layer between the input layer and the output layer, and are each generated through learning processing with multiple data sets acquired for the corresponding imaging target site. The processing circuitry processes first data into second data using, among the neural networks, the neural network corresponding to the imaging target site for the first data. The first data is input to the input layer, and the second data is output from the output layer.

First Embodiment

This embodiment relates to using deep learning (DL) networks or deep neural networks (DNNs) to improve the image quality of reconstructed medical images, and, more particularly, to providing a medical image processing apparatus for realizing DL networks to reduce noise and artifacts in images of reconstructed computed tomography (CT), positron emission tomography (PET), and magnetic resonance imaging (MRI).

To address the above-identified challenges of known reconstruction methods for medical images, the methods described herein have been developed in order to reduce computational time, hardware costs, and further improve image quality low-dose medical images, such as computed tomography (CT) images. Further, the examples provided herein of applying these methods are non-limiting, and the methods described herein can benefit other medical imaging modalities such as MRI, PET/SPECT, etc. by adapting the framework proposed herein. Accordingly, the discussion herein discloses and describes merely exemplary implementations of the present disclosure. As will be understood by those skilled in the art, the present disclosure may be embodied in other specific forms without departing from the spirit or essential characteristics thereof. Accordingly, the present disclosure is intended to be illustrative, but not limiting of the scope of the invention, as well as other claims. The disclosure, including any readily discernible variants of the teachings herein, defines, in part, the scope of the foregoing claim terminology such that no inventive subject matter is dedicated to the public.

In general, it is desirable to reduce CT radiation dose as low as reasonably achievable (ALARA) while maintaining diagnostic quality. Clinical applications for which reduced radiation dose and low-count computed tomography (CT) are advantageous include: CT perfusion study, low and ultra-low-dose CT screening, low dose whole body imaging for melanoma or pediatrics, bias/noise reduction for lower kVp imaging in dual energy CT to reduce total dose, ultra-low-dose CT for PET/CT attenuation correction (CTAC), respiratory-gated CT for phased matched CTAC, and motion correction for PET.

As discussed above, in low-dose CT, the image quality can be degraded by many factors, such as high quanta noise challenge scanning geometry and other non-ideal physical phenomenon. As a result, developing efficient correction methods can be challenging due to the difficulties of modelling an accurate forward model and of solving a complicated inverse problem. For example, model based iterative image reconstruction or sinogram restoration can be time consuming and require expensive hardware.

To address the above-identified challenges of known methods, the methods described herein use deep learning (DL) networks. In general, DL networks have been adapted to image processing area for improving image spatial resolution and reducing noise. As compared to the traditional methods, deep learning does not require accurate noise and edge modelling, relying instead on training data sets. Further, deep learning has the capability to capture the interlayer image features by building up a sophisticated network between noisy observations and latent clean images.

For example, the methods herein leverage improvements in various research areas whereby DL-based convolutional neural network (CNN) can be applied to denoising reconstructed images and/or sinogram restoration. Methods applying DL-based CNN to CT image reconstruction are mostly unknown. Training data corresponding to different CT scanning methods and scanning conditions can be used to train various CNN networks to be tailored for projection data corresponding to particular CT scanning methods, protocols, applications, and conditions by using training data selected to match the particular CT scanning methods, protocols, applications, and conditions. Thus, respective CNN networks can be customized and tailored to certain conditions and methods for CT scanning. Additionally, the customization of the CNN networks can extend to the noise level or to the signal-to-noise ratio of the projection data, and can be extended to the anatomical structure or region of the body being imaged. The methods described herein can be applied to sinogram restoration in addition to denoising of reconstructed images. Further, the redundancy of information in adjacent slices of a three-dimensional CT image can be used to perform volumetric-based DL by using a kernel for the convolution layers of the DL network that extends to pixels in slices above and below a slice that is being denoised. And, in addition to denoising the reconstructed images, the DL can be trained to mitigate artifacts in the reconstructed images.

In particular, various implementations of the methods described herein provide several advantages over previous methods of image reconstruction. First, certain implementations of the methods described herein can use DL to optimize the compensation weights and reconstruction filters in FBP algorithm. For example, in certain implementations, the methods described herein use DL to leverage up analytical reconstruction and provide images with comparable image quality as high-dose model based iterative reconstructions.

Second, certain implementations of the methods described herein perform offline training of a DL network and embed the trained network in the reconstruction step. For example, in certain implementations, the methods described herein can exhibit the benefits associated with: (i) using a three-channel based network; (ii) classifying training data based on noise level; (iii) optimizing the training sets by considering/accounting for the anatomical features; and (iv) classifying training data based on imaging conditions (scan parameters) including a tube voltage, tube current, rotation speed of an X-ray tube, slice thickness for collection, reconstruction function, size of a field of view (FOV), imaging range, reconstruction interval, slice thickness for reconstruction, helical pitch, interpolating reconstruction technique, and so on. Therefore, methods described herein can have better image quality in terms of lower noise and higher spatial resolution than previous methods.

Third, the methods described herein may use images derived from high-dose training data through iterative approximation reconstruction. Accordingly, in certain implementations, clean images similar to those obtained using an iterative reconstruction (IR) method can be achieved by applying the DL network to reconstructed images generated using a less time-intensive reconstruction method (e.g., filtered back-projection), resulting in a dramatic reduction in the computational time and expensive hardware while achieving the image quality of an IR method without the computational burden of an IR method.

In general, DL can be adapted to image processing area for improving image spatial resolution and reducing noise. As compared to the traditional methods, DL does not require accurate noise and edge modelling and only relies on training data sets. Further, DL has the capability to capture the interlayer image features and build up a sophisticated network between noisy observations and latent clean images.

Referring now to the drawings, wherein like reference numerals designate identical or corresponding parts throughout the several views, FIG. 1A shows a flow diagram of method 100, which has two processes: process 110 for offline training and process 140 for reconstructing a high-quality CT image from projection data (which can also be referred to as a sinogram).

The process 110 of method 100 performs offline training of the DL network 135. In step 130 of process 110, noisy data 115 and optimized data 120 are used as training data to train a DL network, resulting in the DL network being output from step 130. More generally, data 115 can be referred to as defect-exhibiting data, for which the "defect" can be any undesirable characteristic that can be affected trough image processing (e.g., noise or an artifact). Similarly, data 120 can be referred to as defect-reduced data, defect-minimized data, or optimize data, for which the "defect" is less than in the data 115. In an example using reconstructed images for data 115 and 120, the offline DL training process 110 trains the DL network 135 using a large number of noisy reconstructed images 115 that are paired with corresponding high-image-quality images 120 to train the DL network 135 to produce images resembling the high-image-quality images from the noisy reconstructed images.

In process 140 of method 100, the projection data 145 is corrected in step 150, and then, in step 160, a CT image is reconstructed from the corrected projection data using an image reconstruction process (e.g., an inverse Radon transformation).

In step 150, the projection data can be corrected for a detector offset (e.g., due to dark current or noise), pile up, variations in quantum efficiency in the detectors (e.g., between detector elements and as a function of energy of the X-ray photons), etc. Further, these corrections can be based on calibration data, empirical, and known parameters (e.g., the geometry of the scanner, the detector elements, anti-scatter grids, etc.).

In step 160, the image reconstruction can be performed using a back-projection method, a filtered back-projection method, a Fourier-transform-based image reconstruction method, an iterative image reconstruction method (e.g., algebraic reconstruction technique), a matrix-inversion image reconstruction method, or a statistical image reconstruction method.

In step 170, the reconstructed image is denoised using the DL network 135. The result of which is a high-quality image 175. Thus, noisy CT images resulting from the CT reconstruction in step 160 can be processed using a DL denoising algorithm applying the network generated by the offline DL training process 110.

Figure 1B:
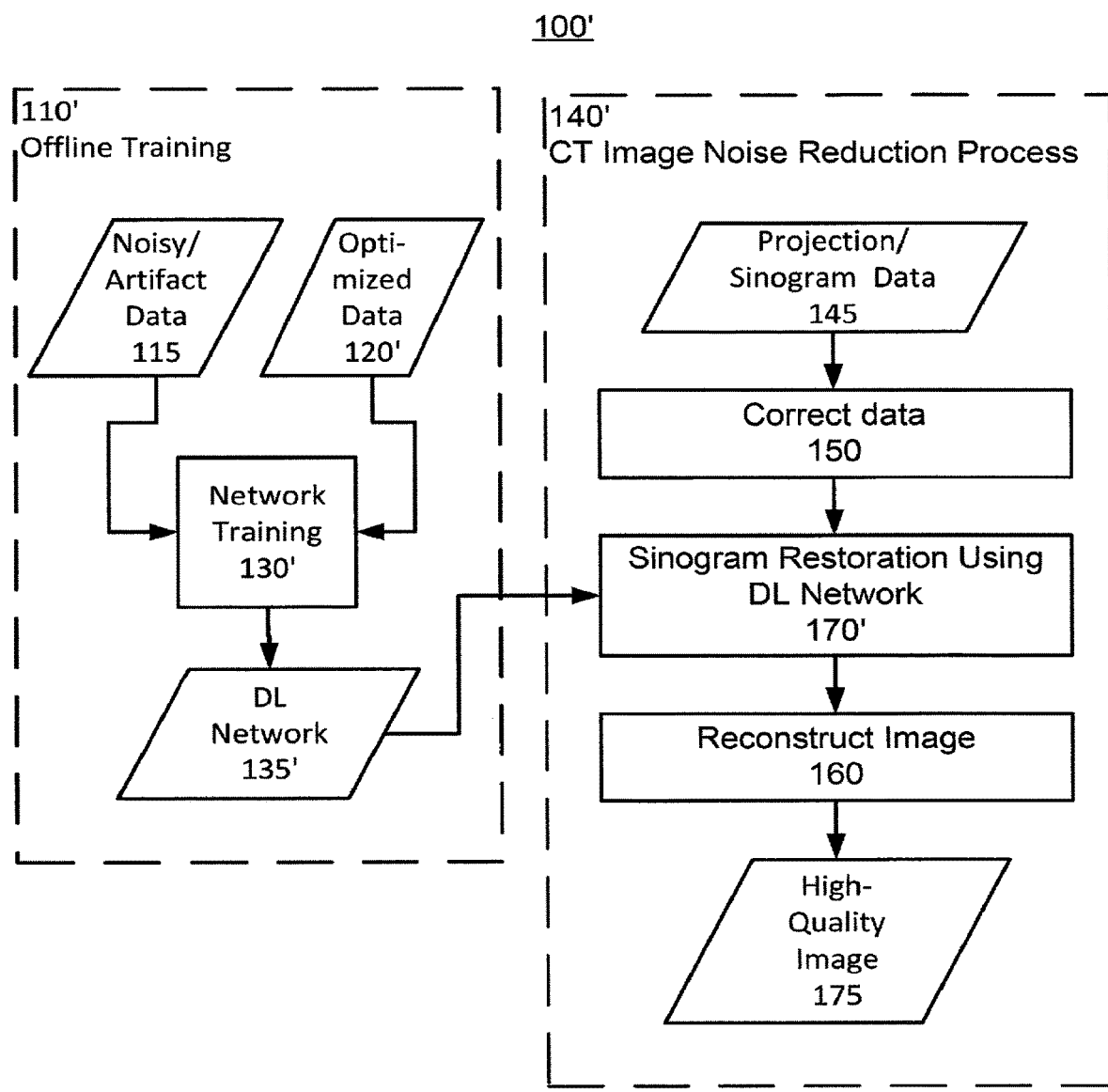
FIG. 1B shows an example of a flow diagram of a method for reducing noise and/or an artifact that uses a DL network to process sinogram data, according to one implementation.

FIG. 1B shows an alternative implementation of method 100. In method 100' shown in FIG. 1B, the DL network 135' is applied in step 170' to restoring the sinogram before the image reconstruction step 160, rather than denoising the reconstructed image after the image reconstruction step 160.

In this case the DL network 135' represents a network that has been trained at step 130' of process 110' using a large number of noisy sinograms 115 that are paired with corresponding high-quality sinograms 120. For example, in step 140', raw data 145 (e.g., pre-log) can be processed by pre-log corrections and converted to sinogram data in step 150. Then, in the sinogram restoration step 170' and the reconstruction step 160, the DL network 135' is applied to sinogram restoration, and, after sinogram correction, image reconstructions are applied to generate the high-quality image 175.

It is also contemplated that in certain implementations a DL network 135' can be used to restore a sinogram and a DL network 135 can be used to denoise the image reconstructed from the restored sinogram within a single method 100 to generate the high-quality image 175.

FIGS. 2A, 2B, 2C, and 2D show various examples of the DL network 135 (135').

Figure 2A:
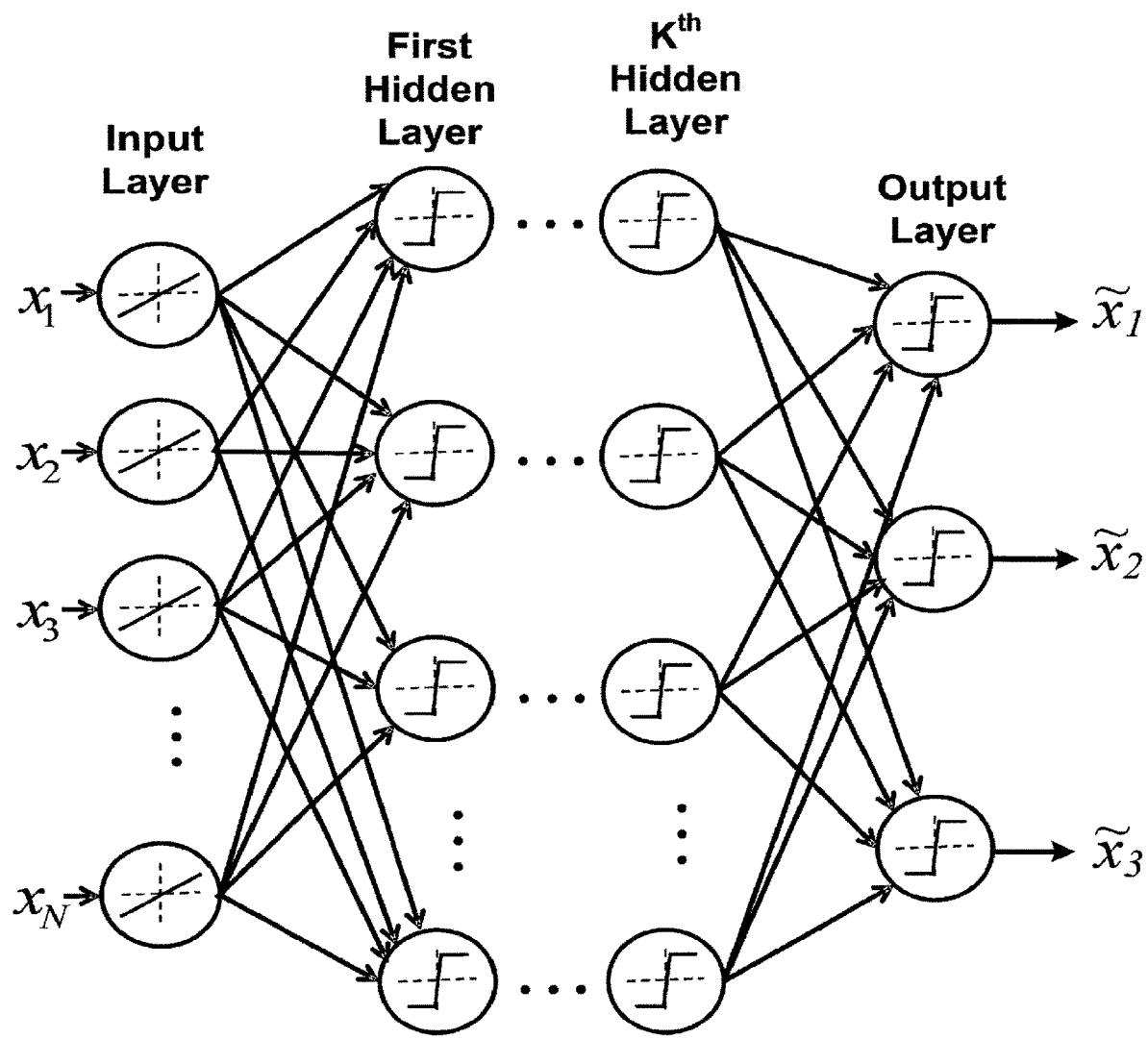
FIG. 2A shows an example of a DL network that is a feedforward artificial neural network (ANN), according to one implementation.

FIG. 2A shows an example of a general artificial neural network (ANN) having N inputs, K hidden layers, and three outputs. Each layer is made up of nodes (also called neurons), and each node performs a weighted sum of the inputs and compares the result of the weighted sum to a threshold to generate an output. ANNs make up a class of functions for which the members of the class are obtained by varying thresholds, connection weights, or specifics of the architecture such as the number of nodes and/or their connectivity. The nodes in an ANN can be referred to as neurons (or as neuronal nodes), and the neurons can have inter-connections between the different layers of the ANN system. The DL network 135 generally has more than three layers of neurons, and has as many outputs neurons $\%$ as input neurons, wherein N is the number of pixels in the reconstructed image (sinogram). The synapses (i.e., the connections between neurons) store values called "weights" (also interchangeably referred to as "coefficients" or "weighting coefficients") that manipulate the data in the calculations. The outputs of the ANN depend on three types of parameters: (i) the interconnection pattern between the different layers of neurons, (ii) the learning process for updating the weights of the interconnections, and (iii) the activation function that converts a neuron's weighted input to its output activation.

Mathematically, a neuron's network function $m(x)$ is defined as a composition of other functions $n_i(x)$, which can further be defined as a composition of other functions. This can be conveniently represented as a network structure, with arrows depicting the dependencies between variables, as shown in FIG. 2. For example, the ANN can use a nonlinear weighted sum, wherein $m(x)=K(\Sigma_i w_i n_i(x))$, where K (commonly referred to as the activation function) is some predefined function, such as the sigmoidal function, hyperbolic tangent function, and rectified linear unit (ReLU).

In FIG. 2A (and similarly in FIG. 2B), the neurons (i.e., nodes) are depicted by circles around a threshold function. For the non-limiting example shown in FIG. 2A, the inputs are depicted as circles around a linear function, and the arrows indicate directed connections between neurons. In certain implementations, the DL network 135 is a feedforward network as exemplified in FIGS. 2A and 2B (e.g., it can be represented as a directed acyclic graph).

The DL network 135 operates to achieve a specific task, such as denoising a CT image, by searching within the class of functions F to learn, using a set of observations, to find $m^* \in F$ which solves the specific task in some optimal sense (e.g., the stopping criteria used in step 260 of step 130 discussed below). For example, in certain implementations, this can be achieved by defining a cost function C:F→iR (??) such that, for the optimal solution m*, C(m*)≤C(m)∀m∈F (i.e., no solution has a cost less than the cost of the optimal solution). The cost function C is a measure of how far away a particular solution is from an optimal solution to the problem to be solved (e.g., the error). Learning algorithms iteratively search through the solution space to find a function that has the smallest possible cost. In certain implementations, the cost is minimized over a sample of the data (i.e., the training data).

Figure 2B:
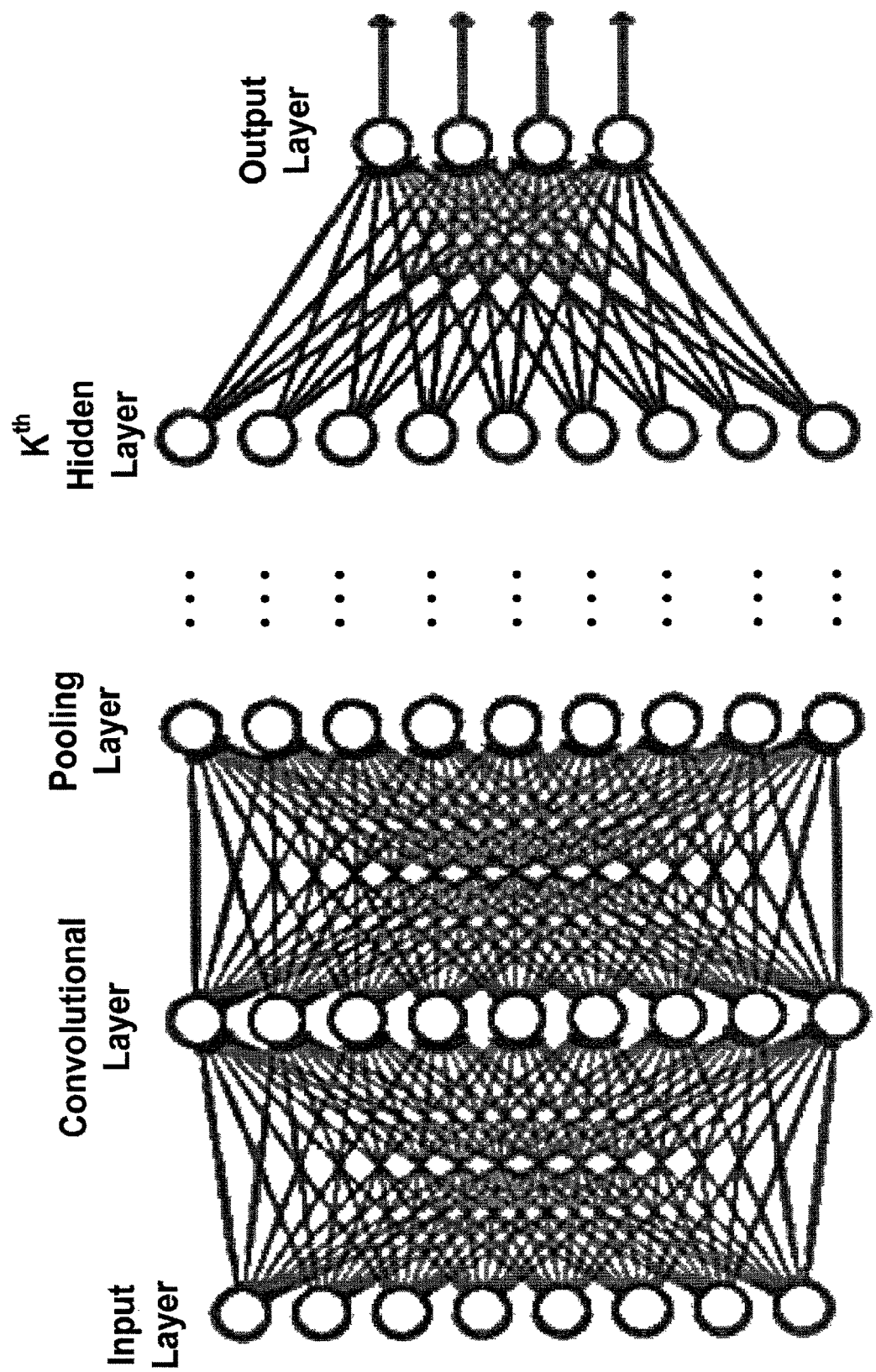
FIG. 2B shows an example of a DL network that is a convolutional neural network (CNN), according to one implementation.

FIG. 2B shows a non-limiting example in which the DL network 135 is a convolutional neural network (CNN). CNNs are type of ANN that has beneficial properties for image processing, and, therefore, have specially relevancy for the applications of image denoising and sinogram restoration. CNNs use feed-forward ANNs in which the connectivity pattern between neurons can represent convolutions in image processing. For example, CNNs can be used for image-processing optimization by using multiple layers of small neuron collections which process portions of the input image, called receptive fields. The outputs of these collections can then tiled so that they overlap, to obtain a better representation of the original image. This processing pattern can be repeated over multiple layers having alternating convolution and pooling layers. Note that FIG. 2B shows an example of a full connect type network defining a node of a succeeding layer using all the nodes of a preceding layer. What is shown in the figure should strictly be understood as one example of DNNs. It is common for CNNs to form a loose connect (partial connect) type network defining a node of a succeeding layer using some of the nodes of a preceding layer.

Figure 2C:
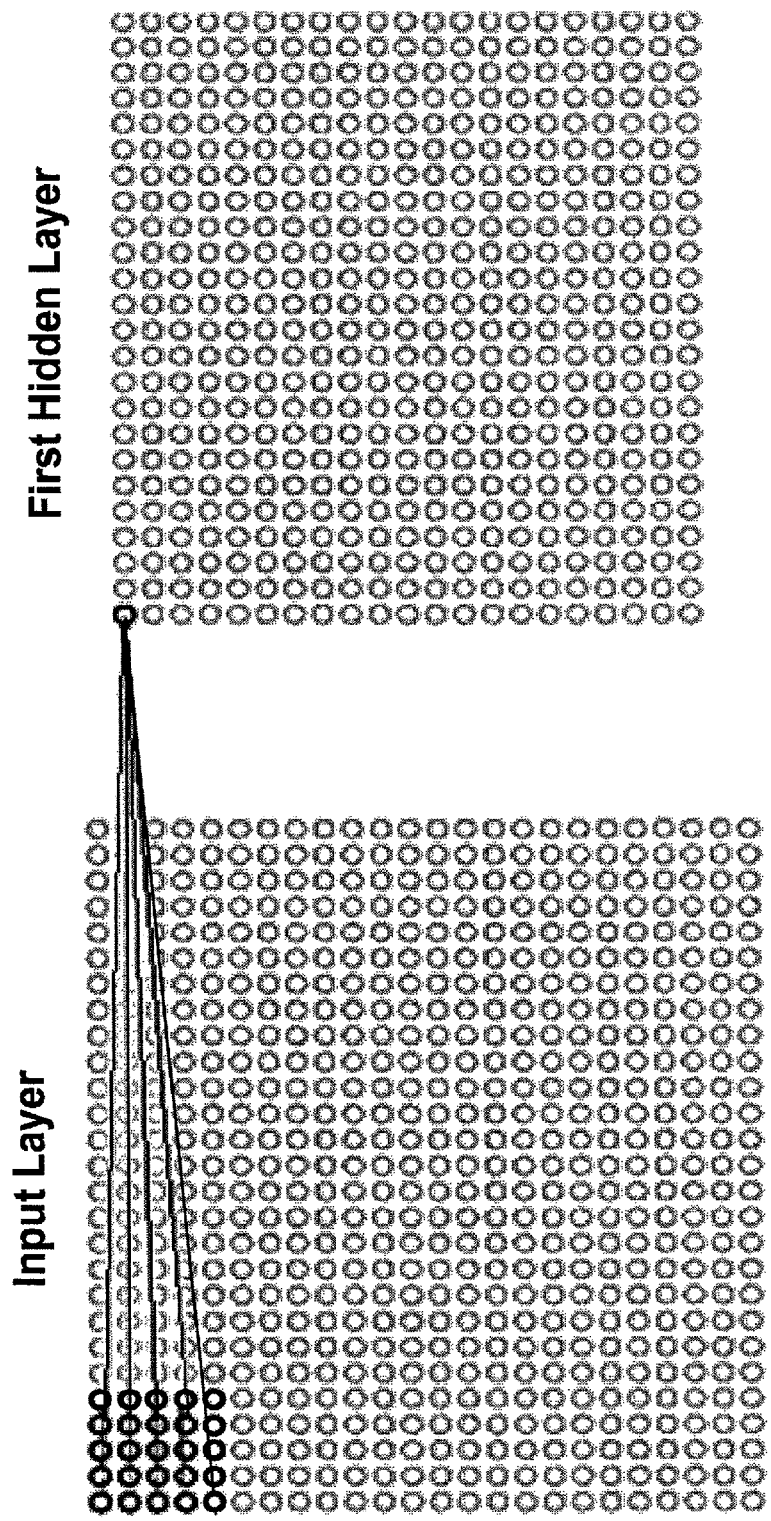
FIG. 2C shows an example of implementing a convolution layer for one neuronal node of the convolution layer, according to one implementation.

FIG. 2C shows an example of a 5×5 kernel being applied to map values from an input layer representing a two-dimensional image to a first hidden layer, which is a convolution layer. The kernel maps respective 5×5 pixel regions to corresponding neurons of the first hidden layer.

Following after a convolutional layer, a CNN can include local and/or global pooling layers, which combine the outputs of neuron clusters in the convolution layers. Additionally, in certain implementations, the CNN can also include various combinations of convolutional and fully connected layers, with pointwise nonlinearity applied at the end of or after each layer.

CNNs have several advantages for image processing. To reduce the number of free parameters and improve generalization, a convolution operation on small regions of input is introduced. One significant advantage of certain implementations of CNNs is the use of shared weight in convolutional layers, which means that the same filter (weights bank) is used as the coefficients for each pixel in the layer; this both reduces memory footprint and improves performance. Compared to other image-processing methods, CNNs advantageously use relatively little pre-processing. This means that the network is responsible for learning the filters that in traditional algorithms were hand-engineered. The lack of dependence on prior knowledge and human effort in designing features is a major advantage for CNNs.

Figure 2D:
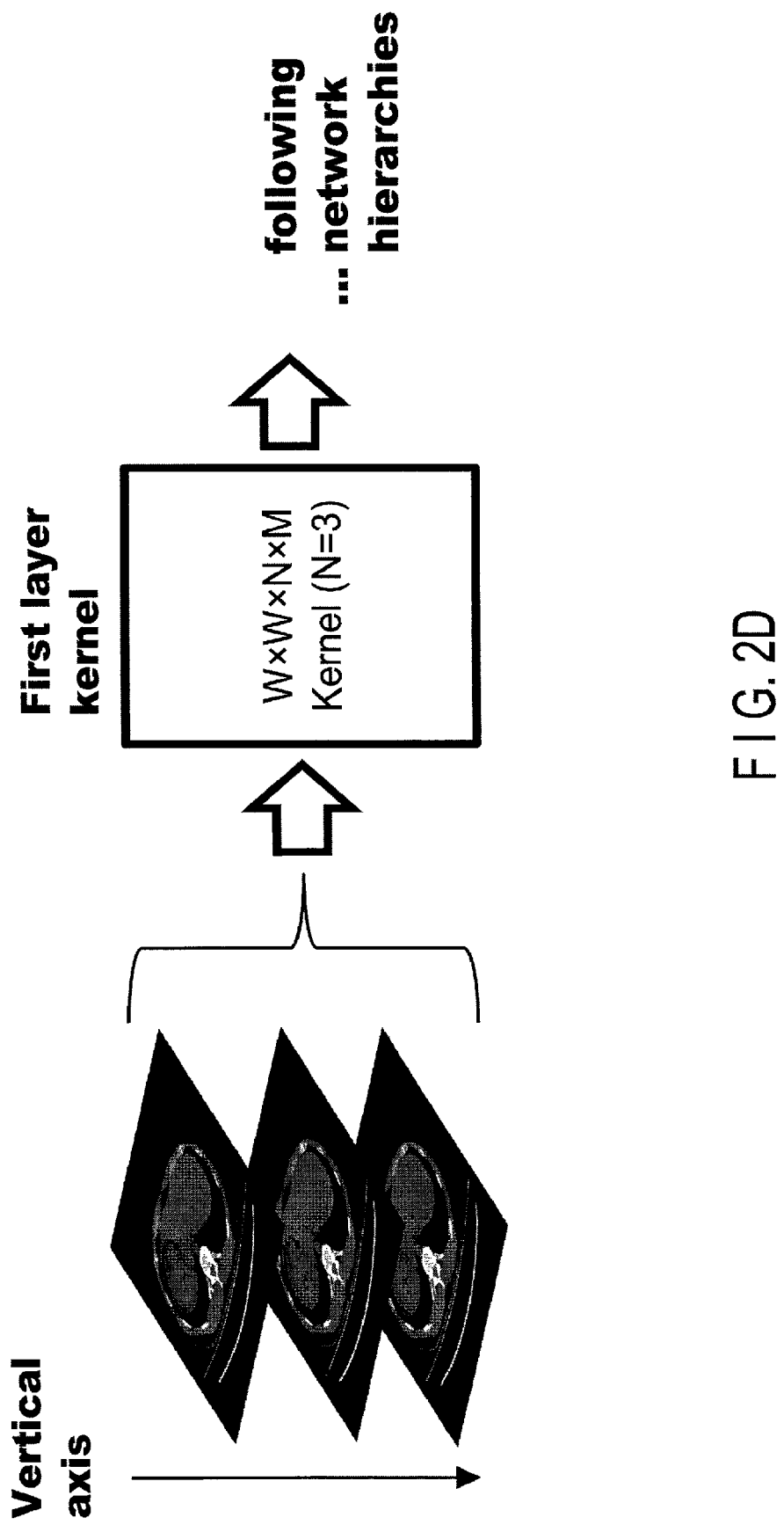
FIG. 2D shows an example of implementing a three channel volumetric convolution layer for volumetric image data, according to one implementation.

FIG. 2D shows an implementation of DL network 135 that takes advantage of the similarities between adjacent layers in reconstructed three-dimensional medical images. The signal in adjacent layers is ordinarily highly correlated, whereas the noise is not. That is, in general, a three-dimensional volumetric image in CT usually can provide more diagnostic information than single slice transverse two-dimensional image since more volumetric features can be captured. Based in this insight, certain implementations of the methods described herein use a volumetric-based deep-learning algorithm to improve the CT images. This insight and corresponding method also applies to other medical imaging areas such as MRI, PET, etc.

As shown in FIG. 2D, a slice and the adjacent slices (i.e., the slice above and below the central slice) are identified as a three-channel input for the network. To these three layers, a W×W×3 kernel is applied M times to generate M values for the convolutional layer, which are then used for the following network layers/hierarchies (e.g., a pooling layer). This W×W×3 kernel can also be thought of and implemented as three W×W kernels respectively applied as three-channel kernels that are applied to the three slices of volumetric image data, and the result is an output for the central layer, which is used as an input for the following network hierarchies. The value M is the total filter number for a given slice of the convolutional layer, and W is the kernel size (e.g., W=5 in FIG. 2C).

In certain implementations, the DL network 135 is not a single network but is instead several networks, each optimized for a different set of conditions of a CT scan. For example, the DL networks 135 can be optimized according to a series of noise classes, corresponding to respective ranges for the signal-to-noise ratio (SNR) or ranges for the noise level. The level of noise relative to the signal in a CT image often depends on the total penetration photon numbers. That is, a high-flux photon number results in higher SNR, whereas a low-flux photon number results in a lower SNR.

Accordingly, capturing the image characteristics at different noise levels can be a beneficial aspect of the offline training process 110, having a significant impact the resulting image quality. Certain implementations of the methods described herein address the differences encountered for different SNRs by training different DL networks 135 according to different ranges of the noise level, especially for low-dose CT image reconstruction.

In the offline training process 110, the noisy images are classified based on their noise level ranges. For each class/range, a separate network of the DL networks 135 is trained. That is, the DL networks 135 include several networks, each corresponding to a specific noise-level range and is trained using noisy images 115 corresponding to the noise-level range.

Then, in the CT image noise reduction step 170, the noise level of the reconstructed image is measured to determine in which noise-level range the reconstructed image belongs. Based on this determination, a corresponding network is selected from the DL networks 135 to perform step 170 for the post processing the reconstructed image. By performing noise-level based training process, the network can be optimized to eliminate the noise texture and artifacts (for example, the streak artifacts in a low-dose scenario) specific to a particular noise level. Ignoring noise level can reduce the image quality and residual undesired noise features might persist.

Additionally, in certain implementations, different networks can be trained for the DL networks 135 based on the type of anatomic features being imaged. To better capture and represent the image features corresponding to different anatomic structures and/or clinical applications, diagnostic images can be optimized using optimized images 120 having qualities tailored to respective clinical applications and/or anatomic structures and, in certain implementations, using tailored optimization strategies and cost functions. For example, the training data can be categorized based on anatomical structures (e.g., head, abdomen, lung, cardiac, etc.). Further, the training data can be further categorized according to anatomical structure. For example, these specially tailored DL networks 135 can be trained using specially generated training data by generating, for each anatomical structure and/or clinical or diagnostic application, pairs of noisy and high-quality images, which are reconstructed for specific anatomical structures and/or with specific reconstruction parameters or kernels for the given clinical or diagnostic purposes.

Then, in step 130, the categories of training data are used to train respective DL networks 135 are trained for different anatomical structure and/or clinical applications. Given the trained DL networks 135, step 170 performs CT image noise reduction using the appropriate trained network(s) selected based on anatomy/application.

Although the above variations for implementing method 100 and method 100' have been exemplified using method 100 to denoise reconstructed images, each variation can also be used with method 100' to restore sinograms prior to image reconstruction in step 160.

Further, method 100 can be used to mitigate artifacts instead of or in addition to denoising reconstructed images. For example, large-angle cone-beam CT (CBCT) scans are desirable for applications benefiting from rapid/short scan times. However, large-angle CBCT can also suffer from various artifacts. When method 100 is tailored for artifact reduction, steps 130 and 170 can be modified as described below.

In step 130, the architecture of the DL network 135 can be modified in order to be optimized for artifact correction by training the DL network 135 using artifact data 115 that exhibits the artifact and artifact free data 120 that is predominantly fee of the artifact. For example, the artifact free data 120 can be generated using a process that is selected to maintain the artifact below a predetermined threshold. In certain implementations, the training data includes high-quality images 120 which can be generated using optimized scan condition (e.g., high dose, small cone angle, with known internal material, etc.) and the corresponding low-quality images 115 can be generated using scan conditions exhibiting the artifact at issue (e.g., the scan conditions and reconstruction process that are anticipated/defaults to be used during the scan used to generate the projection data 145 and the reconstruction method used in step 160). Then the DL networks 135 are trained to remove the artifacts from the low-quality images 115 by optimizing the deep learning architecture of the DL networks 135.

In step 170, the reconstructed image from step 160 is processed using an appropriate network architecture from the DL networks 135 to output the high-quality image 175, which is a high-quality clean image that enables clinicians to make a diagnosis with greater diagnostic confidence. The selected DL network 135 has an appropriate network architecture when the conditions and parameters of the scan and reconstruction giving rise to the reconstructed image generated in step 160 correspond to the conditions and parameters of the data 115 used to train the selected DL network 135.

Consider for example the case of large cone-angle scanning protocols. To reduce the patients motion artifacts and improve image temporal resolution, large cone-angle scanning protocols are often used for head, cardiac and functional CT images. However, due to the angle limitation of incident x-ray beams, the images at a large cone angle position might not have sufficient data to reconstruct certain volume pixels within the reconstructed image volume, resulting in artifacts. Although empirical methods, such as z-axis interpolation, have been proposed to compensate the large cone angle problem, these methods fail to completely eliminate artifacts. To better eliminate the artifacts at large cone angle, a DL network 135 can be optimized and applied in the image domain to reduce the cone beam artifacts. This can be achieved by selecting the training data 115 and 120 to be pairs of images of the same object or patient scanned, in which each pair includes one image using a large-cone-angle protocol and one image using a small-cone-angle protocol (e.g., using helical scans). That is, the artifact data 115 can be generated using the same large-cone-angle protocol that will be used to generate the projection data 145 (e.g., 320 segments), and the optimized data 120 can be generated using a small-cone-angle protocol (e.g., 80 or fewer segments) that maintains the cone-beam artifacts below a predetermined threshold. Then, the DL network 135 will be optimized to correct the artifacts in images reconstructed from projection data 145 generated using a large-cone-angle protocol with 320 segments.

Figure 3:
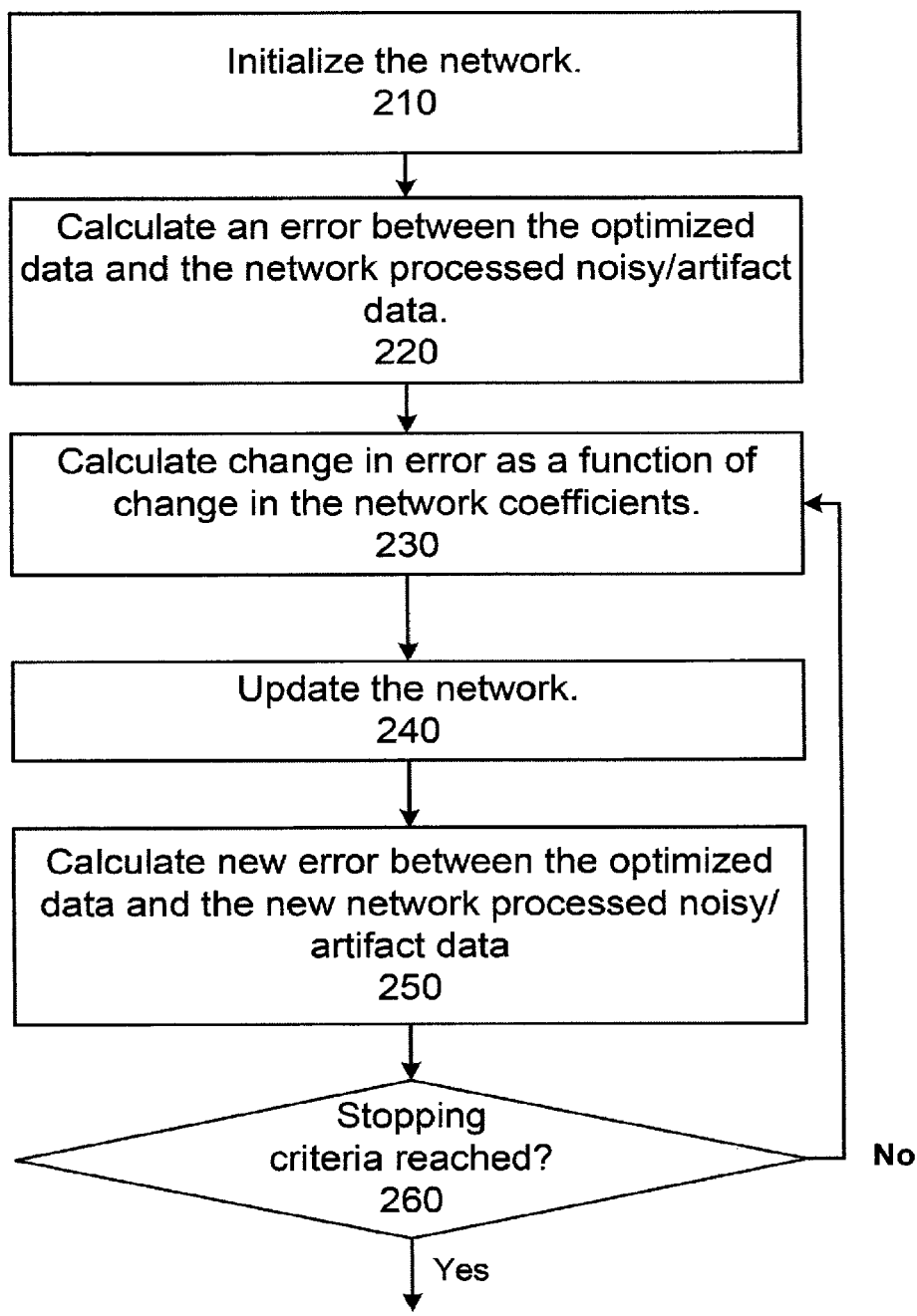
FIG. 3 shows an example of a flow diagram for training a DL network, according to one implementation.

FIG. 3 shows one implementation of supervised learning used to train the DL network 135 in step 130. In supervised learning, a set of training data is obtained, and the network is iteratively updated to reduce the error, such that the noisy data 115 processed by the DL network closely matches the optimized data 120. In other words, DL network infers the mapping implied by the training data, and the cost function produces an error value related to the mismatch between the optimized data 120 and the denoised data produced by applying a current incarnation of the DL network 135 to the noisy data 115. For example, in certain implementations, the cost function can use the mean-squared error to minimize the average squared error. In the case of a of multilayer perceptrons (MLP) neural network, the backpropagation algorithm can be used for training the network by minimizing the mean-squared-error-based cost function using a gradient descent method.

Training a neural network model essentially means selecting one model from the set of allowed models (or, in a Bayesian framework, determining a distribution over the set of allowed models) that minimizes the cost criterion (i.e., the error value calculated using the cost function). Generally, the DL network can be trained using any of numerous algorithms for training neural network models (e.g., by applying optimization theory and statistical estimation).

For example, the optimization method used in training artificial neural networks can use some form of gradient descent, using backpropagation to compute the actual gradients. This is done by taking the derivative of the cost function with respect to the network parameters and then changing those parameters in a gradient-related direction. The backpropagation training algorithm can be: a steepest descent method (e.g., with variable learning rate, with variable learning rate and momentum, and resilient backpropagation), a quasi-Newton method (e.g., Broyden-Fletcher-Goldfarb-Shanno, one step secant, and Levenberg-Marquardt), or a conjugate gradient method (e.g., Fletcher-Reeves update, Polak-Ribiére update, Powell-Beale restart, and scaled conjugate gradient). Additionally, evolutionary methods, such as gene expression programming, simulated annealing, expectation-maximization, non-parametric methods and particle swarm optimization, can also be used for training the DL neural networks 135.

FIG. 3 shows a non-limiting example of a flow diagram of an implementation of step 130 of method 100 (and similarly for step 130' of method 100') for training the network using the training data. The data 115 in the training data can be a noisy image or an image exhibiting an artifact.

For example, an artifact can arise from a particular method of reconstruction, or arise from a method used for acquiring the projection data (e.g., a large-angle cone beam acquisition).

In step 210 of step 130, an initial guess is generated for the coefficients of the DL network 135. For example, the initial guess can be based on a priori knowledge of the region being imaged or one or more exemplary denoising methods, edge-detection methods, and/or blob detection methods. Additionally, the initial guess can be based on a DL network 135 trained on training data related to a different noise level or using a different CT scan method, as discussed above.

Exemplary denoising methods include linear smoothing filters, anisotropic diffusion, non-local means, or nonlinear filters. Linear smoothing filters remove nose by convolving the original image with a mask that represents a low-pass filter or smoothing operation. For example, the Gaussian mask comprises elements determined by a Gaussian function. This convolution brings the value of each pixel into closer agreement with the values of its neighbors. Anisotropic diffusion removes noise while preserving sharp edges by evolving an image under a smoothing partial differential equation similar to the heat equation. A median filter is an example of a nonlinear filter and, if properly designed, a nonlinear filter can also preserve edges and avoid blurring. The median filter is one example of a rank-conditioned rank-selection (RCRS) filter, which can be applied to remove salt and pepper noise from an image without introducing significant blurring artifacts. Additionally, a filter using a total-variation (TV) minimization regularization term can be applied if imaged region supports an assumption of uniformity over large areas that are demarked by sharp boundaries between the uniform areas. A TV filter is another example of a nonlinear filter. Moreover, non-local means filtering is an exemplary method of determining denoised pixels using a weighted average over similar patches within the images.

In step 220 of step 130, an error (e.g., a cost function) is calculated between the network processed noisy data 115 and the optimized data 120. The error can be calculated using any known cost function or distance measure between the image (sinogram) data, including those cost functions described above.

In step 230 of step 130, a change in the error as a function of the change in the network can be calculated (e.g., an error gradient), and this change in the error can be used to select a direction and step size for a subsequent change to the weights/coefficients of the DL network 135. Calculating the gradient of the error in this manner is consistent with certain implementations of a gradient descent optimization method. In certain other implementations, as would be understood by one of ordinary skill in the art, this step can be omitted and/or substituted with another step in accordance with another optimization algorithm (e.g., a non-gradient descent optimization algorithm like simulated annealing or a genetic algorithm).

In step 240 of step 130, a new set of coefficients are determined for the DL network 135. For example, the weights/coefficients can be updated using the changed calculated in step 230, as in a gradient descent optimization method or an over-relaxation acceleration method.

In step 250 of step 130, a new error value is calculated using the updated weights/coefficients of the DL network 135.

In step 260 of step 130, predefined stopping criteria are used to determine whether the training of the network is complete. For example, the predefined stopping criteria can evaluate whether the new error and/or the total number of iterations performed exceed predefined values. For example, the stopping criteria can be satisfied if either the new error falls below a predefined threshold or if a maximum number of iterations is reached. When the stopping criteria is not satisfied process 130 will continue back to the start of the iterative loop by returning and repeating step 230 using the new weights and coefficients (the iterative loop includes steps 230, 240, 250, and 260). When the stopping criteria are satisfied process 130 is completed.

In addition to the implementation for error minimization shown in FIG. 3, process 130 can use one of many other known minimization methods, including, e.g., local minimization methods, convex optimization methods, and global optimization methods.

When the cost function (e.g., the error) has local minima that are different from the global minimum, a robust stochastic optimization process is beneficial to find the global minimum of the cost function. Examples, of optimization method for finding a local minimum can be one of a Nelder-Mead simplex method, a gradient-descent method, a Newton's method, a conjugate gradient method, a shooting method, or other known local optimization method. There are also many known methods for finding global minima including: genetic algorithms, simulated annealing, exhaustive searches, interval methods, and other conventional deterministic, stochastic, heuristic, and metatheuristic methods. Any of these methods can be used to optimize the weights and coefficients of the DL network. Additionally, neural networks can be optimized using a back-propagation method.

Figure 4:
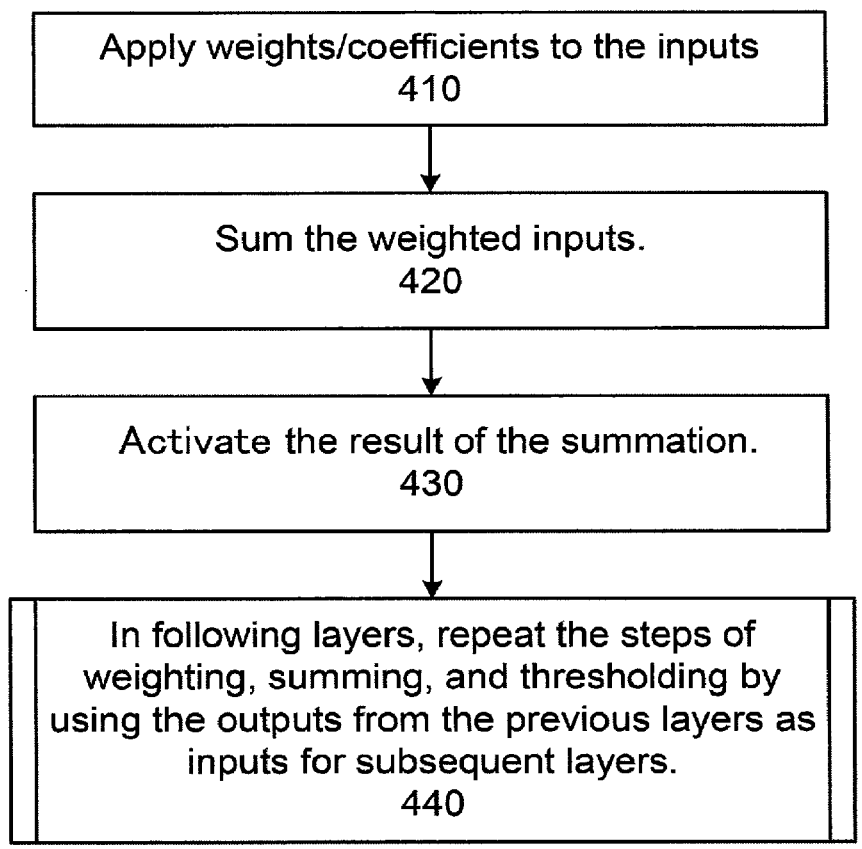
FIG. 4 shows an example of a flow diagram for applying the ANN, according to one implementation.
Figure 5:
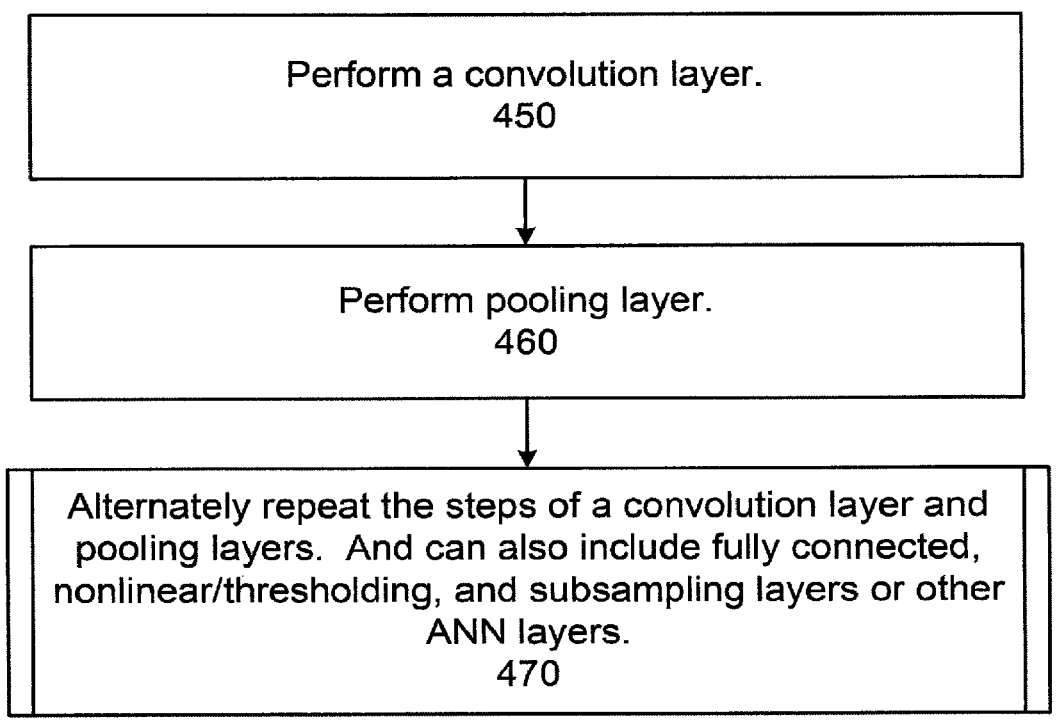
FIG. 5 shows an example of a flow diagram for applying the CNN, according to one implementation.

FIGS. 4 and 5 show flow diagrams of implementations of step 170. FIG. 4 is general for all ANNs, and FIG. 5 is particular to CNNs. Further, FIGS. 4 and 5 are also applicable to step 170' with the substitution that the DL network operates on sinogram data rather than a reconstructed image. The implementation of step 170 shown in FIG. 4 corresponds to applying the DL network 135 to an image that has been reconstructed in step 160. Following after a convolutional layer, a CNN can include local and/or global pooling layers, which combine the outputs of neuron clusters in the convolution layers.

In step 410, the weights/coefficients corresponding to the connections between neurons (i.e., nodes) are applied to the respective inputs corresponding to the pixels of the reconstructed image.

In step 420, the weighted inputs are summed. When the only non-zero weights/coefficients connecting to a given neuron on the next layer are regionally localized in an image represented in the previous layer, the combination of steps 410 and 420 is essentially identical to performing a convolution operation.

In step 430, respective thresholds are applied to the weighted sums of the respective neurons.

In process 440 the steps of weighting, summing, and activating are repeated for each of the subsequent layers.

FIG. 5 shows a flow diagram of another implementation of step 170. The implementation of step 170 (170') shown in FIG. 5 corresponds to operating on the reconstructed image (sinogram data) using a non-limiting implementation of a CNN for the DL network 135.

In step 450, the calculations for a convolution layer are performed as discussed in the foregoing and in accordance with the understanding of convolution layers of one of ordinary skill in the art.

In step 460, the outputs from the convolution layer are the inputs into a pooling layer that is performed according to the foregoing description of pooling layers and in accordance with the understanding of pooling layers of one of ordinary skill in the art.

In process 470 the steps of a convolution layer followed by a pooling can be repeated a predefined number of layers. Following (or intermixed with) the convolution and pooling layers, the output from a pooling layer can be fed to a predefined number of ANN layers that are performed according to the description provided for the ANN layers in FIG. 4. The final out will be a reconstructed image having the desired noise/artifact free characteristics.

Figure 6:
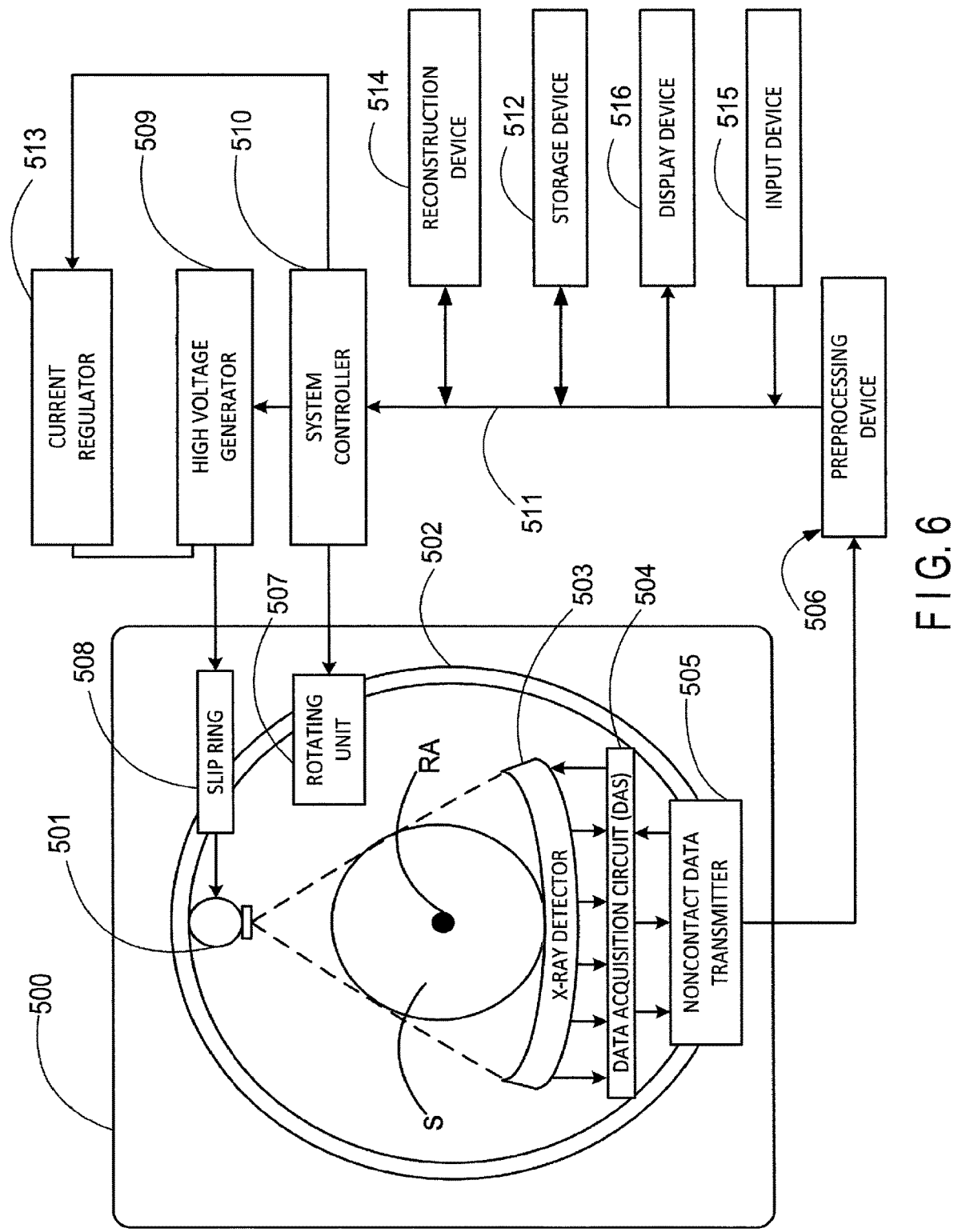
FIG. 6 shows a schematic of an implementation of a computed tomography (CT) scanner, according to one implementation.

FIG. 6 illustrates an implementation of the radiography gantry included in a CT apparatus or scanner. As shown in FIG. 6, a radiography gantry 500 is illustrated from a side view and further includes an X-ray tube 501, an annular frame 502, and a multi-row or two-dimensional-array-type X-ray detector 503. The X-ray tube 501 and X-ray detector 503 are diametrically mounted across an object OBJ on the annular frame 502, which is rotatably supported around a rotation axis RA. A rotating unit 507 rotates the annular frame 502 at a high speed, such as 0.4 sec/rotation, while the object OBJ is being moved along the axis RA into or out of the illustrated page.

The first embodiment of an X-ray computed tomography (CT) apparatus according to the present inventions will be described below with reference to the views of the accompanying drawing. Note that X-ray CT apparatuses include various types of apparatuses, e.g., a rotate/rotate-type apparatus in which an X-ray tube and X-ray detector rotate together around an object to be examined, and a stationary/rotate-type apparatus in which many detection elements are arrayed in the form of a ring or plane, and only an X-ray tube rotates around an object to be examined. The present inventions can be applied to either type. In this case, the rotate/rotate type, which is currently the mainstream, will be exemplified.

The multi-slice X-ray CT apparatus further includes a high voltage generator 509 that generates a tube voltage applied to the X-ray tube 501 through a slip ring 508 so that the X-ray tube 501 generates X-rays. The X-rays are emitted towards the object OBJ, whose cross sectional area is represented by a circle. For example, the X-ray tube 501 having an average X-ray energy during a first scan that is less than an average X-ray energy during a second scan. Thus, two or more scans can be obtained corresponding to different X-ray energies. The X-ray detector 503 is located at an opposite side from the X-ray tube 501 across the object OBJ for detecting the emitted X-rays that have transmitted through the object OBJ. The X-ray detector 503 further includes individual detector elements or units.

The CT apparatus further includes other devices for processing the detected signals from X-ray detector 503. A data acquisition circuit or a Data Acquisition System (DAS) 504 converts a signal output from the X-ray detector 503 for each channel into a voltage signal, amplifies the signal, and further converts the signal into a digital signal. The X-ray detector 503 and the DAS 504 are configured to handle a predetermined total number of projections per rotation (TPPR).

The above-described data is sent to a preprocessing device 506, which is housed in a console outside the radiography gantry 500 through a non-contact data transmitter 505. The preprocessing device 506 performs certain corrections, such as sensitivity correction on the raw data. A memory 512 stores the resultant data, which is also called projection data at a stage immediately before reconstruction processing. The memory 512 is connected to a system controller 510 through a data/control bus 511, together with a reconstruction device 514, input device 515, and display 516. The system controller 510 controls a current regulator 513 that limits the current to a level sufficient for driving the CT system.

The detectors are rotated and/or fixed with respect to the patient among various generations of the CT scanner systems. In one implementation, the above-described CT system can be an example of a combined third-generation geometry and fourth-generation geometry system. In the third-generation system, the X-ray tube 501 and the X-ray detector 503 are diametrically mounted on the annular frame 502 and are rotated around the object OBJ as the annular frame 502 is rotated about the rotation axis RA. In the fourth-generation geometry system, the detectors are fixedly placed around the patient and an X-ray tube rotates around the patient. In an alternative embodiment, the radiography gantry 500 has multiple detectors arranged on the annular frame 502, which is supported by a C-arm and a stand.

The memory 512 can store the measurement value representative of the irradiance of the X-rays at the X-ray detector unit 503. Further, the memory 512 can store a dedicated program for executing various steps of method 100 and/or method 100' for correcting low-count data and CT image reconstruction.

The reconstruction device 514 can execute various steps of method 100 and/or method 100'. Further, reconstruction device 514 can execute pre-reconstruction processing image processing such as volume rendering processing and image difference processing as needed.

The pre-reconstruction processing of the projection data performed by the preprocessing device 506 can include correcting for detector calibrations, detector nonlinearities, and polar effects, for example. Further, the pre-reconstruction processing can include various steps of method 100 and/or method 100'.

Post-reconstruction processing performed by the reconstruction device 514 can include filtering and smoothing the image, volume rendering processing, and image difference processing as needed. The image reconstruction process can implement various of the steps of method 100 and/or method 100' in addition to various CT image reconstruction methods. The reconstruction device 514 can use the memory to store, e.g., projection data, reconstructed images, calibration data and parameters, and computer programs.

The reconstruction device 514 can include a CPU (processing circuitry) that can be implemented as discrete logic gates, as an Application Specific Integrated Circuit (ASIC), a Field Programmable Gate Array (FPGA) or other Complex Programmable Logic Device (CPLD). An FPGA or CPLD implementation may be coded in VHDL, Verilog, or any other hardware description language and the code may be stored in an electronic memory directly within the FPGA or CPLD, or as a separate electronic memory. Further, the memory 512 can be non-volatile, such as ROM, EPROM, EEPROM or FLASH memory. The memory 512 can also be volatile, such as static or dynamic RAM, and a processor, such as a microcontroller or microprocessor, can be provided to manage the electronic memory as well as the interaction between the FPGA or CPLD and the memory.

Alternatively, the CPU in the reconstruction device 514 can execute a computer program including a set of computer-readable instructions that perform the functions described herein, the program being stored in any of the above-described non-transitory electronic memories and/or a hard disk drive, CD, DVD, FLASH drive or any other known storage media. Further, the computer-readable instructions may be provided as a utility application, background daemon, or component of an operating system, or combination thereof, executing in conjunction with a given processor and a given operating system or any operating systems known to those skilled in the art. Further, CPU can be implemented as multiple processors cooperatively working in parallel to perform the instructions.

In one implementation, the reconstructed images can be displayed on a display 516. The display 516 can be an LCD display, CRT display, plasma display, OLED, LED or any other display known in the art.

The memory 512 can be a hard disk drive, CD-ROM drive, DVD drive, FLASH drive, RAM, ROM or any other electronic storage known in the art.

As discussed above, methods 100 and 100' can also be used with positron emission tomography (PET) data or magnetic resonance imaging (MRI) data. Exemplary implementations of MRI and PET scanners are now provided.

Figure 7:
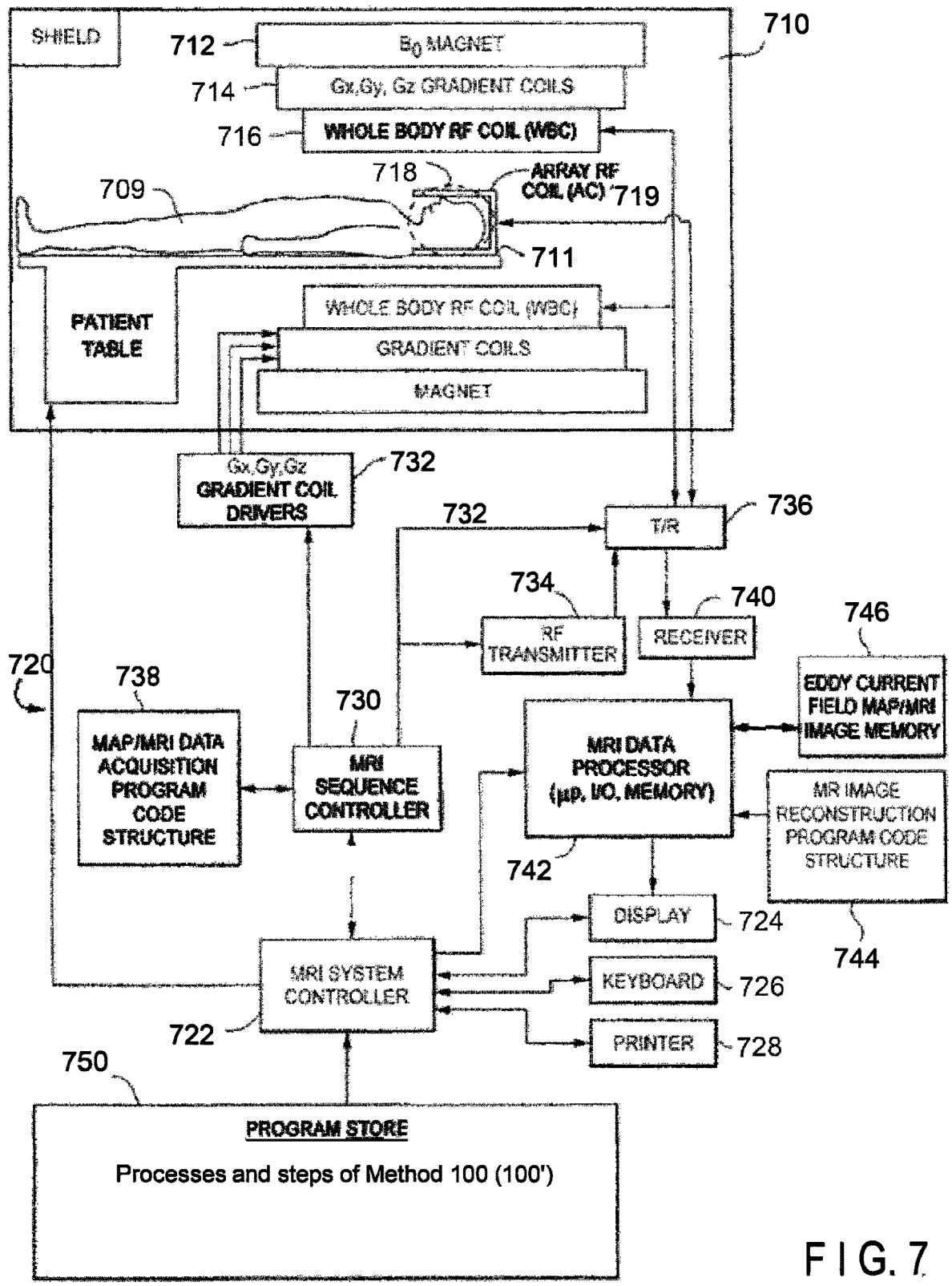
FIG. 7 shows a schematic of an implementation of a magnetic resonance imaging (MRI) scanner, according to one implementation.

Method 100 (100') can also be implemented using MRI data acquired using an MRI scanner such as the non-limiting example of the MRI scanner 700 shown in FIG. 7. MRI is an imaging scan method that magnetically excites nuclear spins of a subject placed in a magnetostatic field by a radio frequency (RF) pulse having a Larmor frequency thereof, to generate an image from magnetic resonance signal data generated with the excitation.

FIG. 7 illustrates a non-limiting example of an exemplary overview of a magnetic resonance imaging (MRI) system 700 according to one or more aspects of the disclosed subject matter. The MRI system 700 includes a gantry 710 (shown in schematic cross section) and various related system components interfaced therewith. At least the gantry 710 is typically located in a shielded room. One MRI system geometry depicted in FIG. 7 includes a substantially coaxial cylindrical arrangement of the static field $B_0$ magnet 712, a Gx, Gy, and Gz gradient coil set 714 and a large whole body RF coil (WBC) assembly 716. The physical Gx, Gy, and Gz gradient axes can be controlled in such a way to create $G_{RO}$, $G_{PE}$, and $G_{SS}$ (readout, phase encode, slice-selection) functional axes. Along the horizontal axis of the cylindrical array of elements is an imaging volume 718 shown as substantially encompassing the chest of a patient 709 supported by a patient table 711. A smaller RF coil 719 is shown as more closely coupled to the head of the patient 709 in image volume 718. RF coil 719 can be a surface coil or array or the like, and can be customized or shaped for particular body parts, such as skulls, arms, shoulders, elbows, wrists, knees, legs, chests, spines, etc. An MRI system controller 722 interfaces with MRI sequence controller 730, which, in turn controls the Gx, Gy, and Gz gradient coil drivers 732, as well as the RF transmitter 734 and the transmit/receive switch 736 (if the same RF coil is used for both transmission and reception). The MRI sequence controller 730 includes suitable program code structure 738 for implementing data acquisition sequences including a fast spin echo (FSE) pulse sequence with a time-shifted $G_{SS}$ gradient, for example. The MRI system controller 722 also can optionally interface with a printer 728, a keyboard 726, and a display 724.

The various related system components include an RF receiver 740 providing input to data processor 742, which is configured to create processed image data, which is then sent to display 724. The MRI data processor 742 is also configured for access to previously acquired data acquisitions of pulse sequences with a time-shifted $G_{SS}$ gradient stored in MRI image memory 746, and to perform various steps of method 100 and/or method 100' stored in code structure 750, as well as MRI image reconstruction program code structure 744.

Also illustrated in FIG. 7 is a generalized depiction of an MRI system program store (memory) 750 where program code structures (e.g., to perform various steps of method 100 and/or method 100', for defining graphical user interfaces and accepting operator inputs to the graphical user interface, etc.) are stored in non-transitory computer-readable storage media accessible to the various data processing components of the MRI system. The program store 750 may be segmented and directly connected, at least in part, to different elements of the various related system components as needed.

Figure 8A:
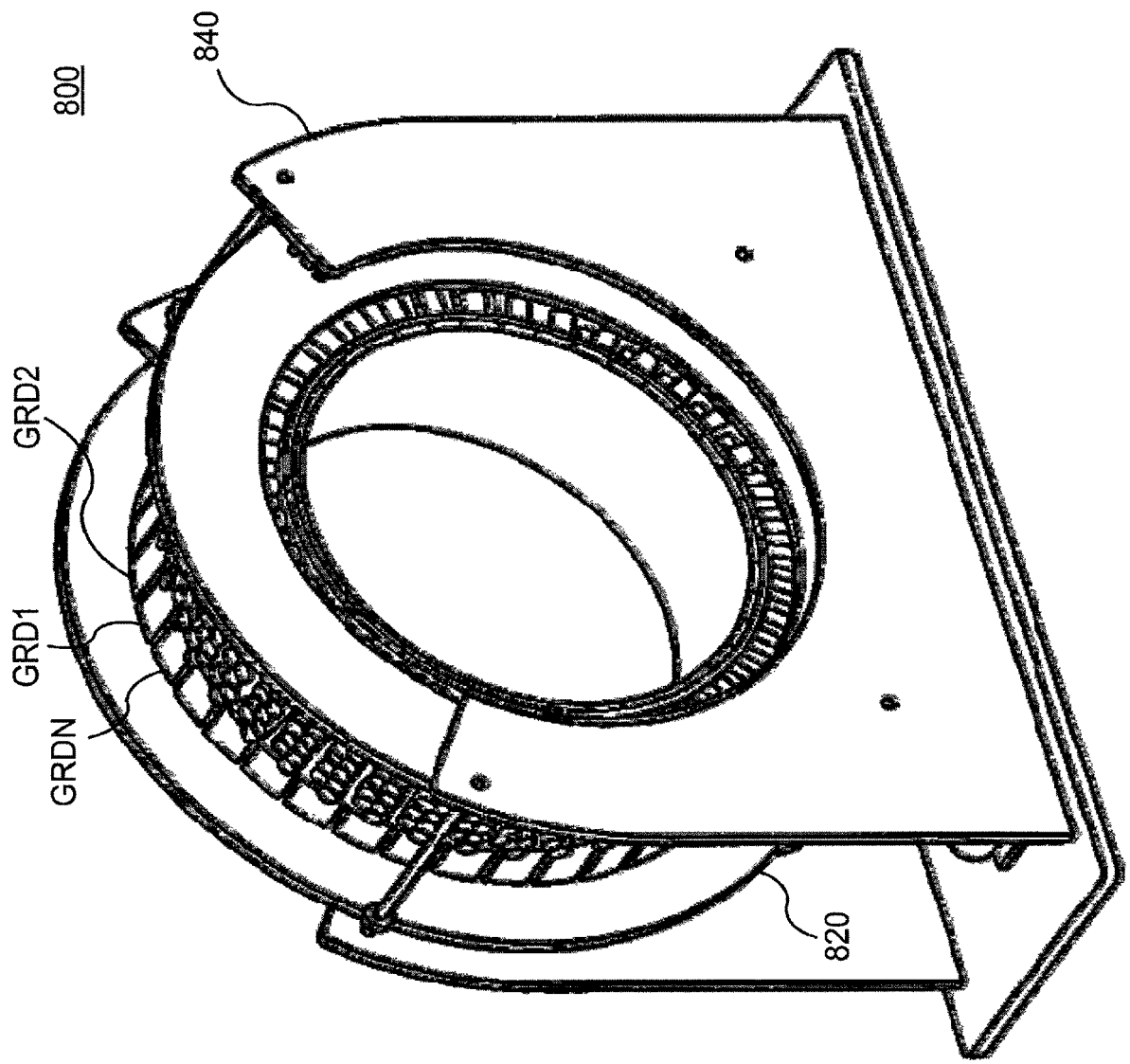
FIG. 8A shows a perspective view of a positron-emission tomography (PET) scanner, according to one implementation.
Figure 8B:
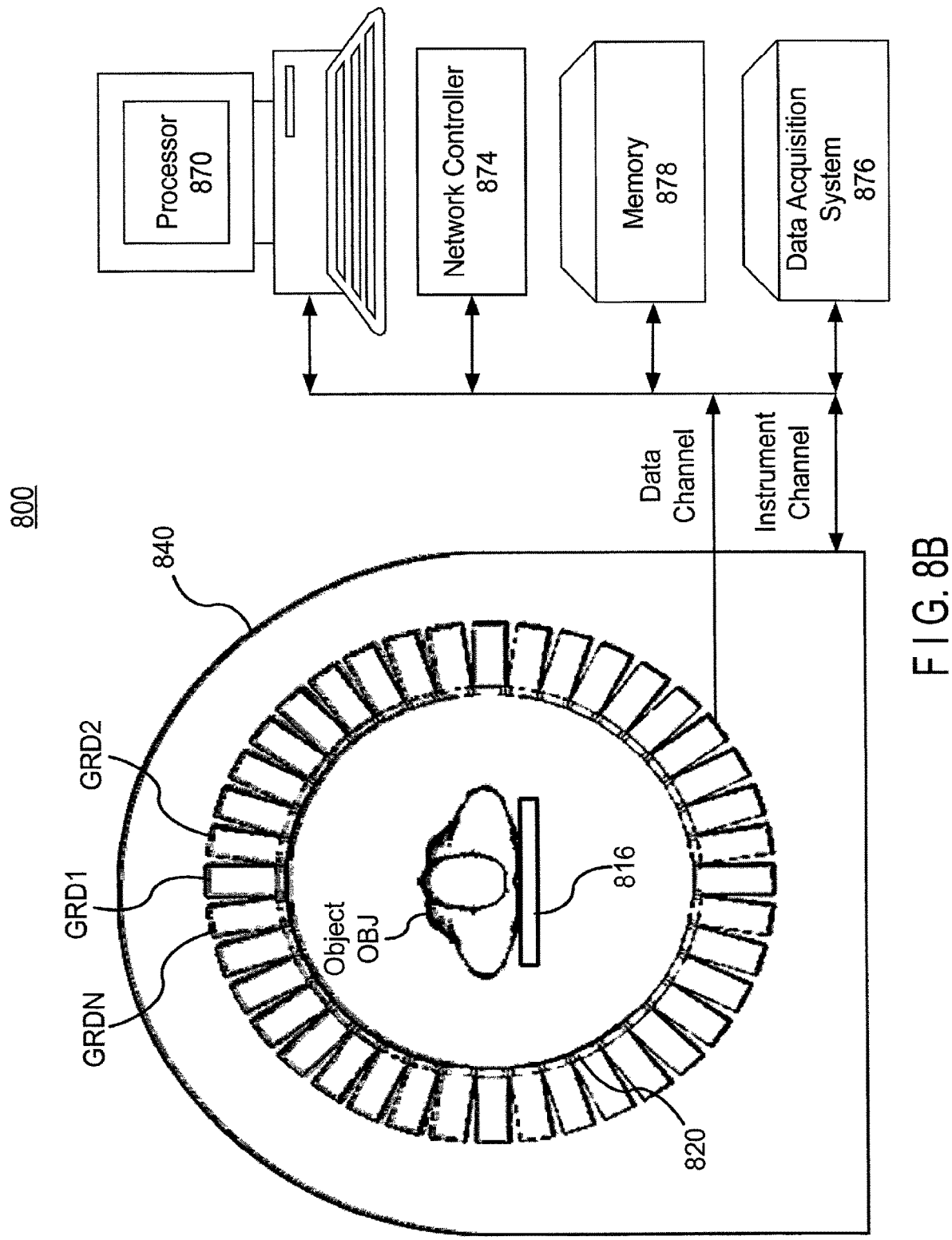
FIG. 8B shows a schematic view of the PET scanner, according to one implementation.

Turning now to an implementation using method 100 (100') using PET data acquired using the non-limiting example of PET scanner 800 shown in FIGS. 8A and 8B. In positron emission tomography (PET) imaging, a radiopharmaceutical agent is introduced into the object to be imaged via injection, inhalation, or ingestion. After administration of the radiopharmaceutical, the physical and bio-molecular properties of the agent cause it to concentrate at specific locations in the human body. The actual spatial distribution of the agent, the intensity of the region of accumulation of the agent, and the kinetics of the process from administration to its eventual elimination are all factors that may have clinical significance. During this process, a positron emitter attached to the radiopharmaceutical agent will emit positrons according to the physical properties of the isotope, such as half-life, branching ratio, etc. The radionuclide emits positrons, and when an emitted positron collides with an electron, an annihilation event occurs, wherein the positron and electron are combined (e.g., an annihilation event can produce two gamma rays (at 511 keV) traveling at substantially 180 degrees apart).

To reconstruct the spatio-temporal distribution of the radio-isotope via tomographic reconstruction principles, each detected event is characterized for its energy (i.e., amount of light generated), its location, and its timing. By detecting the two gamma rays, and drawing a line between their locations, i.e., the line-of-response (LOR), one can determine the likely location of the original disintegration to generate a line of possible interaction. By accumulating a large number of such lines and using a tomographic reconstruction process, a distribution of the radiopharmaceutical agent can be reconstructed. Additional, using accurate timing (within a few hundred picoseconds) a time-of-flight (TOF) calculation can add more information regarding the likely position of the event along the LOR. By collecting a large number of events, an image of an object can be estimated through tomographic reconstruction.

PET imaging systems can use detectors positioned across from one another to detect the gamma rays emitting from the object. A ring of detectors can be used in order to detect gamma rays coming from each angle. Thus, a PET scanner can be substantially cylindrical to be able to capture as much radiation as possible, which should be isotropic. A PET scanner can be composed of several thousand individual crystals (i.e., scintillator elements), which are arranged in two-dimensional scintillator arrays that are packaged in modules with photodetectors to measure the light pulses from respective scintillation events. The relative pulse energy measured by the photodetectors is used to identify the position of the scintillation event. The length or depth of the crystal will determine how likely the gamma ray will be captured. One example of a scintillation crystal is LYSO (or $Lu_{1.8}Y_{0.2}SiO_5$:Ce or Lutetium Orthosilicate). Other crystals can be used.

Using Anger logic and crystal decoding, the source of each scintillation event can be identified as originating from a particular scintillator. A scintillation event will generate light initially radiating isotropically. The spatial distribution of this light may be modified by interactions with scintillator surfaces and reflectors before being detected by the four nearest photodetectors. From the relative pulse energy measured by each of these four photodetectors, the position of the scintillation event relative to the four photodetectors can be determined. The formulas for deriving position information from the relative pulse energies of the photodetectors are referred to as Anger arithmetic. These positions can be further refined by generating a lookup table from a floodmap in order to assign each scintillator event to a scintillator element using the lookup table. This process of mapping from the x- and y-positions obtained using Anger arithmetic to discrete scintillator elements is referred to as crystal decoding.

FIGS. 8A and 8B show a PET scanner 800 including a number of gamma-ray detectors (GRDs) (e.g., GRD1, GRD2, through GRDN) that are each configured as rectangular detector modules. According to one implementation, the detector ring includes 40 GRDs. In another implementation, there are 48 GRDs, and the higher number of GRDs is used to create a larger bore size for the PET scanner 800.

Each GRD can include a two-dimensional array of individual detector crystals, which absorb gamma radiation and emit scintillation photons. The scintillation photons can be detected by a two-dimensional array of photomultiplier tubes (PMTs) that are also arranged in the GRD. A light guide can be disposed between the array of detector crystals and the PMTs. Further, each GRD can include a number of PMTs of various sizes, each of which is arranged to receive scintillation photons from a plurality of detector crystals. Each PMT can produce an analog signal that indicates when scintillation events occur, and an energy of the gamma ray producing the detection event. Moreover, the photons emitted from one detector crystal can be detected by more than one PMT, and, based on the analog signal produced at each PMT, the detector crystal corresponding to the detection event can be determined using Anger logic and crystal decoding, for example.

FIG. 8B shows a schematic view of a PET scanner system having gamma-ray (gamma-ray) photon counting detectors (GRDs) arranged to detect gamma-rays emitted from an object OBJ. The GRDs can measure the timing, position, and energy corresponding to each gamma-ray detection. In one implementation, the gamma-ray detectors are arranged in a ring, as shown in FIGS. 8A and 8B. The detector crystals can be scintillator crystals, which have individual scintillator elements arranged in a two-dimensional array and the scintillator elements can be any known scintillating material. The PMTs can be arranged such that light from each scintillator element is detected by multiple PMTs to enable Anger arithmetic and crystal decoding of scintillation event.

FIG. 8B shows an example of the arrangement of the PET scanner 800, in which the object OBJ to be imaged rests on a table 816 and the GRD modules GRD1 through GRDN are arranged circumferentially around the object OBJ and the table 816. The GRDs can be fixedly connected to a circular component 820 that is fixedly connected to the gantry 840. The gantry 840 houses many parts of the PET imager. The gantry 840 of the PET imager also includes an open aperture through which the object OBJ and the table 816 can pass, and gamma-rays emitted in opposite directions from the object OBJ due to an annihilation event can be detected by the GRDs and timing and energy information can be used to determine coincidences for gamma-ray pairs.

In FIG. 8B, circuitry and hardware is also shown for acquiring, storing, processing, and distributing gamma-ray detection data. The circuitry and hardware include: a processor 870, a network controller 874, a memory 878, and a data acquisition system (DAS) 876. The PET imager also includes a data channel that routes detection measurement results from the GRDs to the DAS 876, a processor 870, a memory 878, and a network controller 874. The data acquisition system 876 can control the acquisition, digitization, and routing of the detection data from the detectors. In one implementation, the DAS 876 controls the movement of the bed 816. The processor 870 performs functions including reconstructing images from the detection data, pre-reconstruction processing of the detection data, and post-reconstruction processing of the image data, as discussed herein.

The processor 870 can be configured to perform various steps of method 100 and/or 100' described herein. The processor 870 can include a CPU that can be implemented as discrete logic gates, as an Application Specific Integrated Circuit (ASIC), a Field Programmable Gate Array (FPGA) or other Complex Programmable Logic Device (CPLD). An FPGA or CPLD implementation may be coded in VHDL, Verilog, or any other hardware description language and the code may be stored in an electronic memory directly within the FPGA or CPLD, or as a separate electronic memory. Further, the memory may be non-volatile, such as ROM, EPROM, EEPROM or FLASH memory. The memory can also be volatile, such as static or dynamic RAM, and a processor, such as a microcontroller or microprocessor, may be provided to manage the electronic memory as well as the interaction between the FPGA or CPLD and the memory.

Alternatively, the CPU in the processor 870 can execute a computer program including a set of computer-readable instructions that perform various steps of method 100 and/or method 100', the program being stored in any of the above-described non-transitory electronic memories and/or a hard disk drive, CD, DVD, FLASH drive or any other known storage media. Further, the computer-readable instructions may be provided as a utility application, background daemon, or component of an operating system, or combination thereof, executing in conjunction with a given processor and a given operating system or any operating systems known to those skilled in the art. Further, CPU can be implemented as multiple processors cooperatively working in parallel to perform the instructions.

The memory 878 can be a hard disk drive, CD-ROM drive, DVD drive, FLASH drive, RAM, ROM or any other electronic storage known in the art.

The network controller 874 can interface between the various parts of the PET imager. Additionally, the network controller 874 can also interface with an external network. As can be appreciated, the external network can be a public network, such as the Internet, or a private network such as an LAN or WAN network, or any combination thereof and can also include PSTN or ISDN sub-networks. The external network can also be wired, or can be wireless. The wireless network can also be any given wireless form of communication that is known.

Second Embodiment

Next, a medical image processing apparatus according to a second embodiment will be described.

Generally, noise granularity of reconstructed images (e.g., granular and random noise texture attributable to concentration variations on the images) is influenced by imaging conditions such as, in particular, the size of a field of view (FOV), a reconstruction function, and an X-ray dose.

For example, provided that the same imaging conditions including the reconstruction function and the matrix size, except the FOV size, are adopted for a given imaging site, a smaller FOV will have a coarse granularity. Reconstruction processing, especially when using a noise model, is often susceptible to the granularity due to a difference in FOV size. In this relation, assuming that imaging sites are bones, it would normally be the case that the same (or proximate) reconstruction functions are adopted for these sites. However, the FOV size to be selected differs also depending on the site where a targeted bone exists, for example, a size of 70 mm to 100 mm would be selected for imaging a bone in an internal ear part, a size of 50 mm to 100 mm would be selected for imaging a bone in extremities, and a size of 100 mm to 150 mm would be selected for imaging a vertebra. Consequently, the reconstructed images for display will have different noise granularities even when the same reconstruction functions are used. As such, the resulted difference in noise granularity could degrade the workability in observation operations as hampering, for example, comparative verification of multiple images obtained by performing imaging processes with different FOV sizes for a given site or sites for diagnosis.

Moreover, an optimal reconstruction function and an FOV to be set vary depending on where the imaging site is, e.g., abdomen, lung, chest, or head. The reconstructed images for display will accordingly have different noise granularities for respective imaging sites. On the other hand, doctors involved in image reading might desire the same level of noise granularity for the reconstructed images for observation, irrespective of the differences in imaging site.

This embodiment therefore adopts a reconstruction device 514 that includes a plurality of DNNs addressing a plurality of different-sized FOVs, and that is adapted to input reconstructed images to the DNNs for corresponding FOV sizes and to output reconstructed images having the same level (user's desired level) of noise granularity not dependent on the FOV sizes.

Note that the functions that will be explained in relation to this embodiment may be implemented in addition to, or separately from, the functions having been explained for the first embodiment. Also, the input layer, the intermediate layer, and the output layer of a DNN, the activation functions to select, the weighting coefficients to select, the configurations to utilize a CNN, and so on may be adopted in the present embodiment in the manner as explained for the first embodiment. Training of DNNs in the context of the present embodiment will be explained later.

Figure 9:
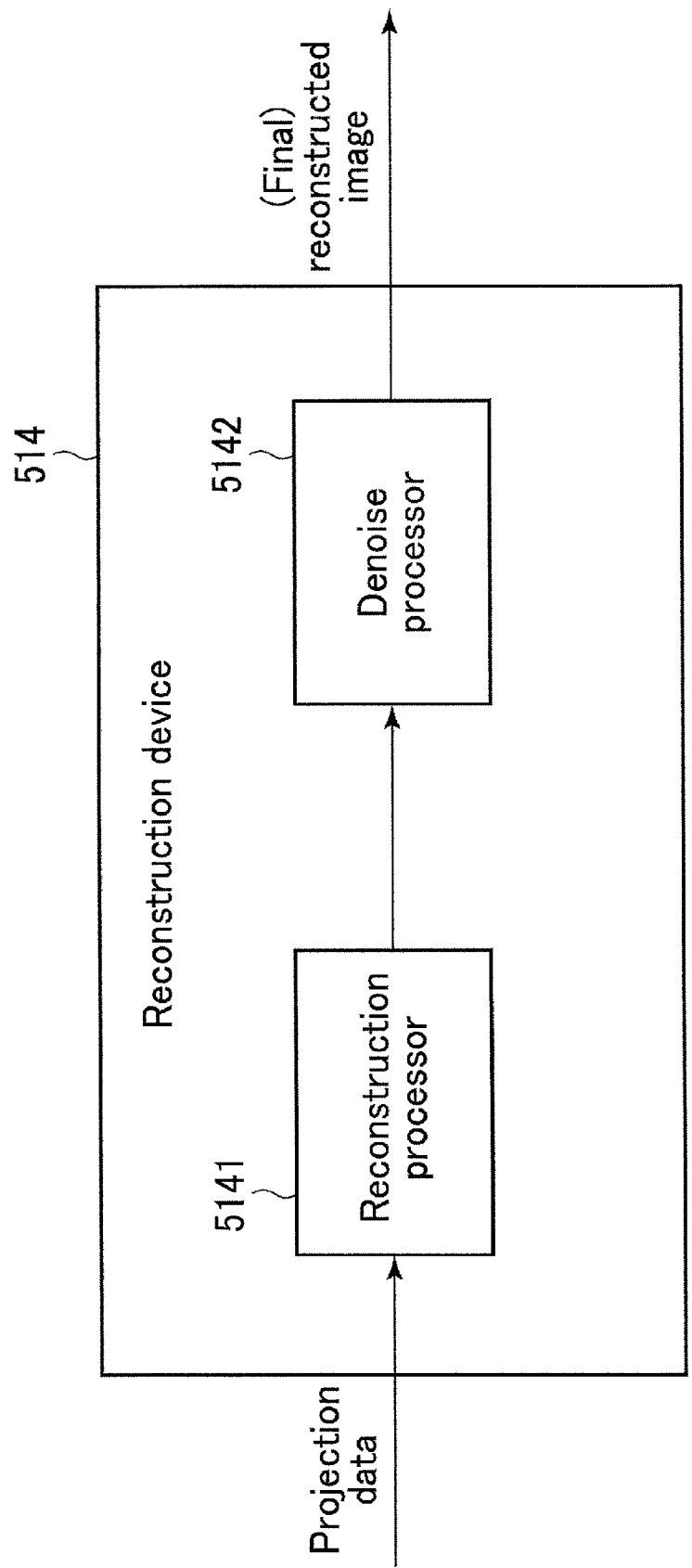
FIG. 9 is a block diagram for a reconstruction device according to a second embodiment.

FIG. 9 is a block diagram for the reconstruction device 514 according to the present embodiment. As shown in the figure, the reconstruction device 514 includes a reconstruction processor 5141 and a denoise processor 5142. The reconstruction processor 5141 and the denoise processor 5142 each have the configuration and function as will be described.

(Configuration and Function of the Reconstruction Processor 5141)

The reconstruction processor 5141 performs two-stage noise reduction processing with noise models, i.e., on projection data and on image data, in order to reduce noise and artifacts so that reconstructed images with high S/N ratio and enhanced texture are generated. The processing performed by the reconstruction processor 5141 may also be combined with the noise reduction processing described for the first embodiment.

Figure 10:
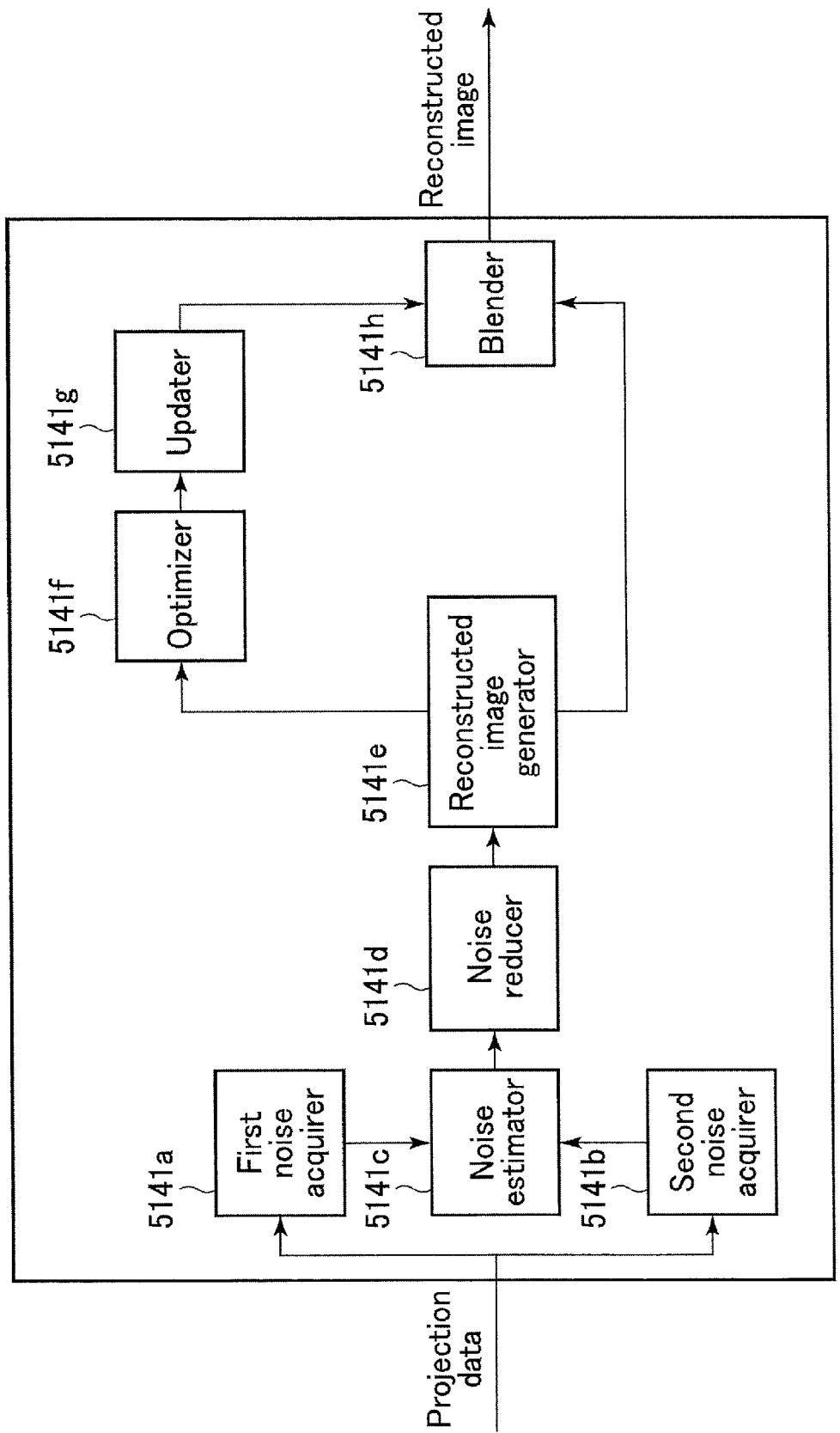
FIG. 10 is a block diagram showing an exemplary overview configuration of a reconstruction processor according to the second embodiment.

FIG. 10 is a block diagram showing an example of an overview configuration of the reconstruction processor 5141. As shown in the figure, the reconstruction processor 5141 includes a first noise acquirer 5141a, a second noise acquirer 5141b, a noise estimator 5141c, a noise reducer 5141d, a reconstructed image generator 5141e, an optimizer 5141f, an updater 5141g, and a blender 5141h.

The first noise acquirer 5141a estimates an amount of noise by applying a system model (a scanner model, etc., that takes into account the unique characteristics of a device, such as a device geometry) to projection count data before logarithmic conversion.

The second noise acquirer 5141b estimates an amount of noise by applying a statistical noise model (a noise model that statistically takes into account the photon noise and electrical noise in each X-ray dose band) to the projection count data before logarithmic conversion.

The noise estimator 5141c obtains the total amount of estimated noise related to the projection count data before logarithmic conversion, based on the respective noise amounts estimated by the first noise acquirer 5141a and the second noise acquirer 5141b.

The noise reducer 5141d performs noise reduction processing for the projection count data before logarithmic conversion in accordance with the noise amount obtained by the noise estimator 5141c. The noise reducer 5141d further performs logarithmic conversion, etc. for this noise-reduced projection count data and outputs the resultant data.

The reconstructed image generator 5141e performs reconstruction processing for the projection data (after the noise reduction processing and the logarithmic conversion) received from the noise reducer 5141d to generate a reconstructed image. This reconstruction processing performed by the reconstructed image generator 5141e may adopt iterative approximation reconstruction (full IR), filtered back-projection (FBP), or a combination thereof (hybrid processing).

The optimizer 5141f performs optimization processing with an anatomical model for the reconstructed image received from the reconstructed image generator 5141e, or for an updated reconstructed image fed back from the updater 5141g, so that noise present on the image data is selectively removed while the structure is retained with high sharpness using three dimensional information. The optimizer 5141f also performs predetermined smoothing processing for the reconstructed image received from the reconstructed image generator 5141e.

The updater 5141g performs update processing for the reconstructed image using the optimized image data and the smoothed image data output from the optimizer 5141f. The updated reconstructed image is output back to the optimizer 5141f. The optimizer 5141f and the updater 5141g repeat these optimization processing, smoothing processing, and update processing until predetermined conditions are met.

The blender 5141h blends the reconstructed image output from the updater 5141g with the (initial) reconstructed image output from the reconstructed image generator 5141e in a predetermined ratio so that the noise granularity is maintained on the image data while the S/N ratio is improved, and therefore, a reconstructed image having more natural texture is produced.

Note that how many times the respective processing between the optimizer 5141f and the updater 5141g should be repeated, and what blending ratio the blender 5141h should adopt for its blend processing may be determined according to imaging sites, clinical applications, etc.

(Configuration and Function of the Denoise Processor 5142)

The denoise processor 5142 of FIG. 9 includes a plurality of DNNs addressing a plurality of different-sized FOVs. The denoise processor 5142 receives reconstructed images of various FOV sizes from the reconstruction processor 5141, and performs denoise processing by the DNNs to output reconstructed images having the same level of noise granularity not dependent on the FOV sizes. The denoise processing performed by the denoise processor 5142 is, however, not limited to the denoise processing related to FOV sizes, but may adopt different denoise processing in combination.

FIG. 11 is a block diagram showing an example of the overview configuration of the denoise processor 5142. As shown in this figure, the denoise processor 5142 includes a network selector 5142a and a first DNN group 5142b.

The network selector 5142a receives a reconstructed image and FOV size information output from the reconstruction processor 5141, selects a DNN for use in the denoise processing based on the FOV size of the reconstructed image, and outputs the reconstructed image to the selected DNN.

The first DNN group 5142b is formed by a DNN 5142b1 to a DNN 5142bn for addressing respective, n-staged FOV sizes, i.e., FOV size 1 to an FOV size n. Each DNN 5142bi (where i is an integer satisfying $1 \leq i \leq n$) performs denoise processing (processing for realizing a uniform noise granularity level) in which it receives the input of a reconstructed image of the FOV size i conforming to its own stage, and outputs a reconstructed image having a predetermined noise granularity (irrespective of the FOV size).

FIG. 12 is a block diagram showing another example of the overview configuration of the denoise processor 5142. The denoise processor 5142 shown in this figure includes the network selector 5142a, and a first DNN group 5142b to an m-th DNN group 5142z for addressing respective, m-staged noise granularity levels, i.e., noise granularity level 1 to noise granularity level m.

The network selector 5142a of this example selects an applicable DNN group from among the first DNN group 5142b to the m-th DNN group 5142z based on a desired noise granularity level. Also, the network selector 5142a receives a reconstructed image and FOV size information output from the reconstruction processor 5141, further selects a DNN for use in the denoise processing from the selected DNN group (the one selected based on the noise granularity level) based on the FOV size of the reconstructed image, and outputs the reconstructed image to the selected DNN.

In this relation, the desired noise granularity level may be obtained through a configuration in which it is input by a manual operation of a user via the input device 515, or a configuration in which it is automatically selected according to an imaging site, reconstruction function, etc., input as the imaging conditions. Such configurations of enabling the noise granularity to be discretionarily selected with reference to imaging sites, reconstruction functions, etc., are particularly beneficial in improving image qualities and promoting the efficiency in image observations.

The first DNN group 5142b to the m-th DNN group 5142z address the respective noise granularity levels 1 to m, and are each formed by n DNNs for addressing respective, n-staged FOV sizes, i.e., FOV sizes 1 to n. Each of the DNNs 5142bi to zi (where i is an integer satisfying $1 \leq i \leq n$) performs denoise processing (processing for realizing a uniform noise granularity level) in which it receives the input of a reconstructed image of the FOV size i conforming to its own stage, and outputs a reconstructed image having a predetermined noise granularity (irrespective of the FOV size).

(Training of DNNs)

Training (supervised training) of each DNN included in the denoise processor 5142 according to this embodiment is performed by preparing many patterns of training samples, which are formed of pairs of a reconstructed image as the input data having the noise granularity that follows its own FOV size assigned and a reconstructed image as the output data having an optimum noise granularity level irrespective of the FOV size, and by optimizing the network parameters using these training samples as training data.

Figure 13:
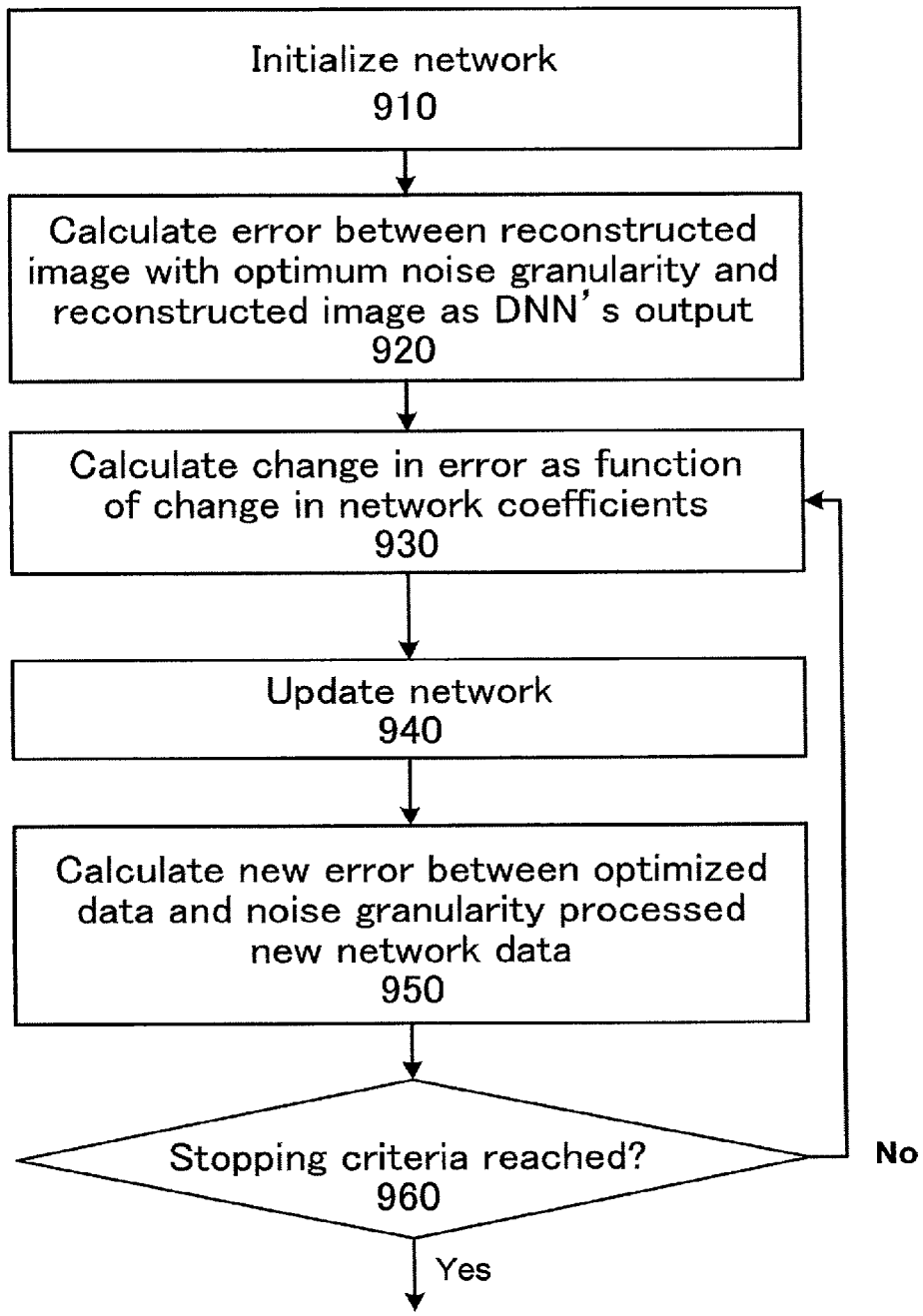
FIG. 13 is a flowchart showing a training flow for each DNN shown in FIGS. 11 and 12.

FIG. 13 is a flowchart showing a training flow for each of the DNNs shown in FIGS. 11 and 12. Steps 910, 920, 930, 940, 950, and 960 shown in FIG. 13 correspond substantially to the respective steps 210, 220, 230, 240, 250, and 260 shown in FIG. 3. These steps may each be described in a similar manner to the steps described with reference to FIG. 3, but the outlines are as follows.

As shown in FIG. 13, each parameter of the training target DNN is initialized (step 910), and an error between a reconstructed image having an optimum noise granularity irrespective of the FOV size and a reconstructed image as the DNN's output is calculated (step 920). A change in the calculated error is calculated as a function of the change in coefficients of the DNN using an algorithm such as the stochastic gradient-descent method (step 930), and the DNN is updated using the calculated function of the change (step 940). Further, an error between the reconstructed image having an optimum noise granularity irrespective of the FOV size and a reconstructed image as an output from the DNN updated in step 940 is calculated (step 950). Whether or not a change in the calculated error satisfies the stopping criteria is determined, and if yes, the network parameters for the DNN are fixed (step 960, Yes). If the change in the calculated error does not satisfy the stopping criteria, steps 930 to 950 are repeated so that the network parameters are optimized (step 960, No).

Modification

The functions of the reconstruction device 514, discussed for the first embodiment and the second embodiment above, may be realized also by a medical image processing system configured with a client and a server with a network therebetween.

Figure 14:
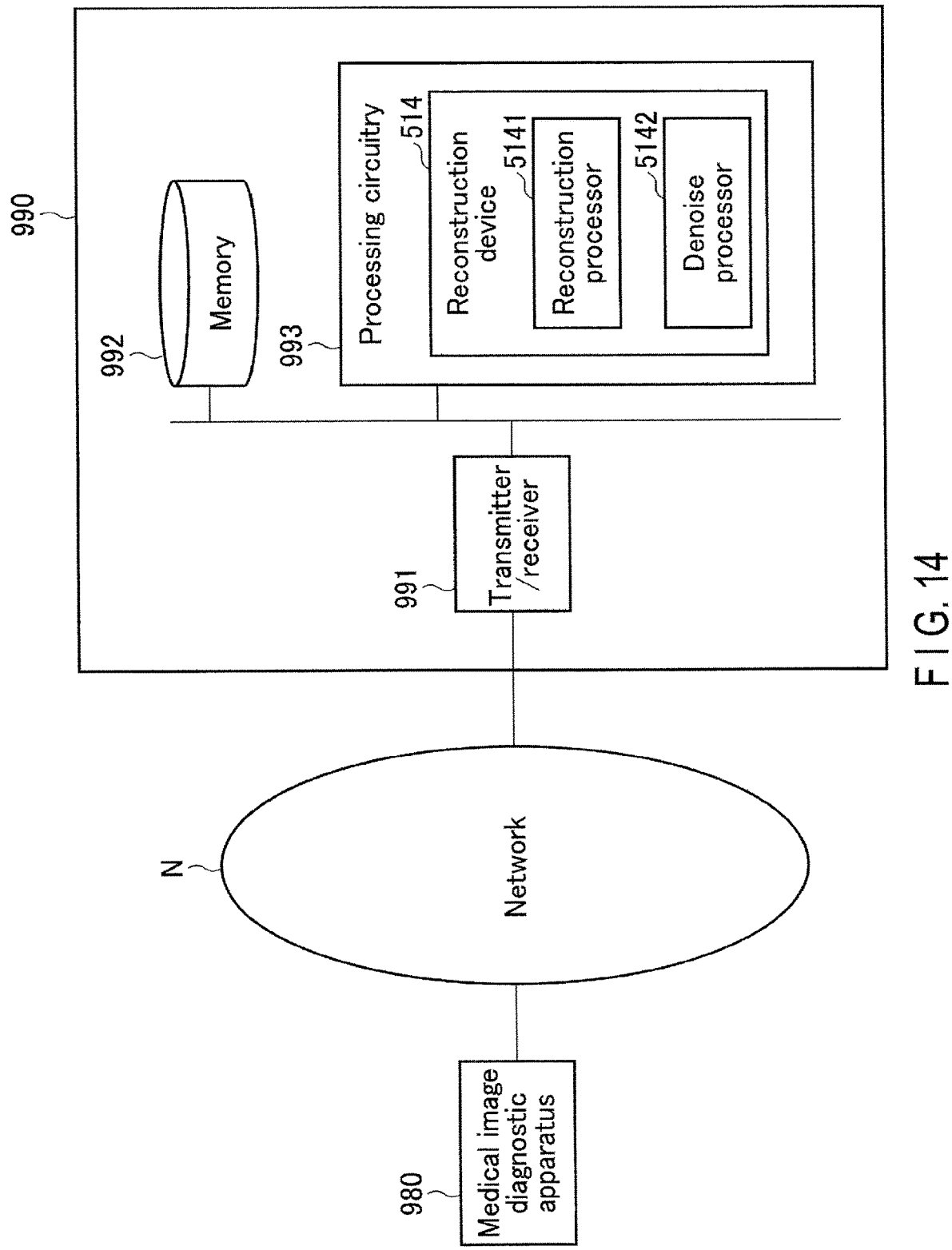
FIG. 14 shows an example of a medical image processing system that has a client-server configuration involving an intermediary network.

FIG. 14 shows an example of a medical image processing system 970 that has a client-server configuration involving an intermediary network. As shown in this figure, the medical image processing system 970 includes a medical image diagnostic apparatus 980 as a client-side apparatus, and a medical image processing apparatus 990 as a server-side apparatus connected with the medical image diagnostic apparatus 980 via a network N.

The medical image diagnostic apparatus 980 may typically be an X-ray CT apparatus as shown in FIG. 6, an MRI apparatus as shown in FIG. 7, a PET apparatus as shown in FIGS. 8A and 8B, and so on.

The medical image processing apparatus 990 includes a transmitter/receiver 991, a memory 992, and processing circuitry 993. The transmitter/receiver 991 transmits data to, and receives data from, the medical image diagnostic apparatus 980 via the network N. The memory 992 stores information such as medical image data received from the medical image diagnostic apparatus 980, and various dedicated programs for executing the reconstruction processing, denoise processing, etc. as described. The processing circuitry 993 is a processor to realize the functions of the reconstruction device 514 as described.

With these configurations, the medical image diagnostic apparatus 980 is not required to implement the functions of the reconstruction device 514. Therefore, the processing load within the medical image diagnostic apparatus 980 as well as the costs associated with the medical image diagnostic apparatus 980 can be reduced. Also, the reconstruction processing and the denoise processing are performed in a uniform manner in the medical image processing apparatus 990 as a server side. Thus, it is possible to avoid variations in image qualities, etc. that might otherwise occur due to differences in operators when the reconstruction processing and the denoise processing are performed in each local medical image diagnostic apparatus.

Effects

According to the configurations having been disclosed, even in the instances where reconstructed images have different levels of noise granularity due to differences in FOV size, it is possible to output reconstructed images having the same level (user's desired level) of noise granularity irrespective of the FOV sizes. The disclosed configurations allow for the selection of any noise granularity levels for final reconstructed images in accordance with imaging sites, etc. Users can discretionarily obtain reconstructed images that show their desired noise granularity levels. Accordingly, the disclosed configurations can provide images which are easy to compare, and can contribute to the improved workability of doctors involved in image reading.

Also, according to a certain embodiment, the reconstruction processor 5141 is adapted to perform noise reduction processing using a noise model, before the denoise processor 5142 performs processing for a uniform noise granularity level. Accordingly, streak artifacts can be reduced in advance of the processing by the denoise processor 5142. As a result, the DNNs are not required to include a layer for reducing streak artifacts, and the layer structures of the DNNs can be downsized.

While certain implementations and embodiments have been described, they have been presented by way of example only, and are not intended to limit the teachings of this disclosure. Indeed, the novel methods, apparatuses and systems described herein may be embodied in a variety of other forms; furthermore, various omissions, substitutions and changes in the form of the methods, apparatuses and systems described herein may be made without departing from the spirit of this disclosure.

The invention claimed is:

1. A medical image processing apparatus comprising:
a memory storing a plurality of neural networks corresponding to a plurality of imaging target sites, respectively, the neural networks each including an input layer, an output layer, and an intermediate layer between the input layer and the output layer, and each generated through learning processing with multiple data sets acquired for the corresponding imaging target site; and
processing circuitry configured to process a plurality of sets of first data acquired using respective different field-of-view (FOV) sizes corresponding to one of the plurality of imaging target sites into respective sets of second data each of which has a granularity level independent of the FOV size, each of the sets of first data being processed using a corresponding one of the plurality of neural networks,
wherein for the one of the plurality of neural networks corresponding to the imaging target site, the corresponding set of the first data is input to the input layer and the corresponding set of the second data is output from the output layer.

2. The medical image processing apparatus according to claim 1, wherein
the memory is configured to store a plurality of neural networks corresponding to a plurality of imaging conditions, respectively, the neural networks corresponding to the respective imaging conditions each including an input layer, an output layer, and an intermediate layer between the input layer and the output layer, and each generated through learning processing with multiple data sets acquired under imaging conditions equal to or similar to the corresponding imaging condition; and
the processing circuitry is configured to process the second data into third data using, among the neural networks corresponding to the respective imaging conditions, the neural network corresponding to the imaging condition for the second data, wherein the second data is input to the input layer and the third data is output from the output layer.

3. The medical image processing apparatus according to claim 1, wherein
the memory is configured to store a plurality of neural networks corresponding to a plurality of noise levels, respectively, the neural networks corresponding to the respective noise levels each including an input layer, an output layer, and an intermediate layer between the input layer and the output layer, and each generated through learning processing with multiple data sets having noise levels equal to or similar to the corresponding noise level; and
the processing circuitry is configured to process the second data into third data using, among the neural networks corresponding to the respective noise levels, the neural network corresponding to the noise level of the second data, wherein the second data is input to the input layer and the third data is output from the output layer.

4. The medical image processing apparatus according claim 1, wherein the first data is data before reconstruction.

5. The medical image processing apparatus according to claim 1, wherein the first data is reconstructed image data.

6. The medical image processing apparatus according to claim 5, wherein
the memory is configured to store a plurality of neural networks corresponding to the FOV sizes, respectively, the neural networks corresponding to the respective FOV sizes each including an input layer, an output layer, and an intermediate layer between the input layer and the output layer, and each generated through learning processing with multiple data sets acquired for the corresponding FOV size, and
the processing circuitry is configured to process the second data into third data using, among the neural networks corresponding to the respective FOV sizes, the neural network corresponding to the FOV size of the second data, wherein the second data is input to the input layer and the third data is output from the output layer.

7. The medical image processing apparatus according to claim 5, wherein the first data comprises data corresponding to a first slice plane, data corresponding to a second slice place, and data corresponding to a third slice plane, the second slice plane and the third slice plane adjacent the first slice plane with respect to a slice direction, and the neural networks are convolutional neural networks each using a kernel with channels corresponding to the first slice plane, the second slice plane, and the third slice plane.

8. The medical image processing apparatus according to claim 1, wherein the multiple data sets for the learning processing comprise multiple pre-denoised data sets, and multiple denoised data sets corresponding to the respective pre-denoised data sets.

9. The medical image processing apparatus according to claim 1, wherein the multiple data sets for the learning processing comprise multiple pre-artifact removed data sets, and multiple artifact removed data sets corresponding to the respective pre-artifact removed data sets.

10. The medical image processing apparatus according to claim 1, wherein the multiple data sets for the learning processing comprise multiple pre-noise granularity processed data sets, and multiple noise granularity processed data sets corresponding to the respective pre-noise granularity processed data sets.

11. The medical image processing apparatus according to claim 1, wherein the processing circuitry is configured to perfoiiii noise reduction processing for the first data or the second data based on noise estimated using a geometry of an imaging system and noise estimated using a statistical noise model.

12. The medical image processing apparatus according to claim 1, wherein the processing circuitry is configured to use three dimensional information to retain a sharp structure in the first data or the second data and selectively remove noise.

13. A medical image processing system comprising a server apparatus and a client apparatus, wherein the server apparatus comprises:
  a memory storing a plurality of neural networks corresponding to a plurality of imaging target sites, respectively, the neural networks each including an input layer, an output layer, and an intermediate layer between the input layer and the output layer, and each generated through learning processing with multiple data sets acquired for the corresponding imaging target site; and
  processing circuitry configured to process a plurality of sets of first data acquired using respective different field-of-view (FOV) sizes corresponding to one of the plurality of imaging target sites into respective sets of second data each of which having a granularity level independent of the FOV size using one of the plurality of neural networks, wherein for the one of the plurality of neural networks corresponding to the imaging target site, the corresponding set of the first data is input to the input layer and the corresponding set of the second data is output from the output layer, and the client apparatus is configured to receive the second data via a network.

14. The medical image processing apparatus according to claim 1, wherein the imaging condition includes a size of a field of view, a reconstruction function, or an x-ray dose used for acquiring the first data.

15. The medical image processing apparatus according to claim 1, wherein
  the memory storing the plurality of neural networks including multiple neural networks corresponding to a plurality of FOV sizes for one of the plurality of imaging target sites, and
  the processing circuitry is configured to process a set of first data acquired using a certain FOV size into a set of second data, based on one of the multiple neural networks corresponding to the first FOV size.

16. A medical image processing apparatus comprising:
  a memory storing a plurality of neural networks corresponding to a plurality of field-of-view (FOV) sizes, respectively, the neural networks each including an input layer, an output layer, and an intermediate layer between the input layer and the output layer, and each generated through learning processing with multiple data sets acquired for the corresponding FOV size; and
  processing circuitry configured to process a plurality of sets of first data acquired using respective different FOV sizes into respective sets of second data each of which having a granularity level independent of the FOV size using the neural networks,
  wherein for a neural network corresponding to the FOV size, the corresponding set of the first data is input to the input layer and the corresponding set of the second data is output from the output layer.

* * * * *